US011266752B2

(12) United States Patent
Wrenn et al.

(10) Patent No.: US 11,266,752 B2
(45) Date of Patent: *Mar. 8, 2022

(54) METHODS OF IMAGING AND DELIVERING THERAPEUTIC AGENTS

(71) Applicant: DREXEL UNIVERSITY, Philadelphia, PA (US)

(72) Inventors: Steven Wrenn, Swarthmore, PA (US); Brett Angel, Bala Cynwyd, PA (US); Andrew Kohut, Philadelphia, PA (US); Aaron Fafarman, Narberth, PA (US); Michael Cimorelli, Turnersville, NJ (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/403,429

(22) Filed: Aug. 16, 2021

(65) Prior Publication Data
US 2021/0379209 A1    Dec. 9, 2021

Related U.S. Application Data

(63) Continuation of application No. 17/204,561, filed on Mar. 17, 2021, which is a continuation of application No. 16/858,329, filed on Apr. 24, 2020, now Pat. No. 10,980,898, which is a continuation of application No. 16/029,335, filed on Jul. 6, 2018, now abandoned.

(60) Provisional application No. 62/529,700, filed on Jul. 7, 2017.

(51) Int. Cl.
| | | |
|---|---|---|
| *A61K 41/00* | (2020.01) | |
| *A61K 9/00* | (2006.01) | |
| *A61K 49/22* | (2006.01) | |
| *A61B 8/08* | (2006.01) | |
| *A61K 9/107* | (2006.01) | |
| *A61K 9/127* | (2006.01) | |
| *A61N 1/40* | (2006.01) | |

(52) U.S. Cl.
CPC .......... *A61K 49/227* (2013.01); *A61B 8/0883* (2013.01); *A61B 8/481* (2013.01); *A61K 9/0009* (2013.01); *A61K 9/1075* (2013.01); *A61K 9/127* (2013.01); *A61K 41/0028* (2013.01); *A61N 1/40* (2013.01)

(58) Field of Classification Search
CPC ........ A61K 49/227; A61K 9/00; A61K 9/127; A61K 9/1075; A61K 41/00
See application file for complete search history.

(56) References Cited

U.S. PATENT DOCUMENTS

| | | | |
|---|---|---|---|
| 5,827,533 A | 10/1998 | Needham | |
| 5,846,518 A | 12/1998 | Yan et al. | |
| 6,041,252 A | 3/2000 | Walker et al. | |
| 6,041,253 A | 3/2000 | Kost et al. | |
| 6,183,725 B1 | 2/2001 | Yan et al. | |
| 6,613,306 B1* | 9/2003 | Schneider | A61K 49/223 424/9.51 |
| 6,638,767 B2* | 10/2003 | Unger | A61P 9/10 435/458 |
| 8,257,691 B2 | 9/2012 | Eliaz et al. | |
| 2008/0063603 A1 | 3/2008 | Schneider et al. | |
| 2009/0155345 A1 | 6/2009 | Barenholz et al. | |
| 2012/0109045 A1 | 5/2012 | Wrenn et al. | |
| 2012/0244078 A1 | 9/2012 | Rychak | |
| 2014/0243391 A1 | 8/2014 | Lebeau et al. | |
| 2014/0271822 A1 | 9/2014 | McGhee et al. | |
| 2015/0273407 A1* | 10/2015 | Gil | B01D 69/144 210/650 |

FOREIGN PATENT DOCUMENTS

| | | |
|---|---|---|
| JP | 2010260828 A | 11/2010 |
| JP | 2014058469 A | 4/2014 |
| WO | 9625955 A1 | 8/1996 |
| WO | 2014140670 A1 | 9/2014 |

OTHER PUBLICATIONS

International Search Report and Written Opinion for PCT International Application No. PCT/US2018/041095 dated Nov. 21, 2018.
"Extended European Search Report for European Patent Appln. No. 18828923.5 dated Mar. 29, 2021".
"Liposome", https://en.wikipedia.org/w/index.php?title=Liposome&oldid=736240037 <retrieved Sep. 10, 2018>, Aug. 2016, 7 Pages.
Aliabouzar, et al., "Acoustic vaporization threshold of lipid-coated perfluoropentane droplets", The Journal of the Acoustical Society of America, 143, Apr. 2018, 2001-2012.
Bartolomeo, et al., "Nesting microbubbles: influence on acoustic activity and image brightness", Bubble Science Engineering and Technology, 2012. 4(2): p., Sep. 2012, 78-84 (Abstract Only).
Cimorelli, et al., "Introducing a nested phase change agent with an acoustic response that depends on electric field: A candidate for myocardial perfusion imaging and drug delivery", Applied Acoustics, vol. 138; XP055787376, Mar. 30, 2021, 9-17.
Dicker, et al., "Coencapsulation of lipid microbubbles within polymer microcapsules for contrast applications", Bubble Science Engineering and Technology 3(1), Mar. 2011, 12-19 (Abstract Only).
Dicker, et al., "Determination of microbubble cavitation threshold pressure as function of shell chemistry", Bubble Science Engineering and Technology, 2010. 2(2), 2010, 55-64 (Abstract Only).
Dicker, et al., "Influence of shell composition on the resonance frequency of microbubble contrast agents", Ultrasound Med Biol. 39(7), Jul. 2013, 1292-1302 (Abstract Only).

(Continued)

*Primary Examiner* — Michael G. Hartley
*Assistant Examiner* — Jagadishwar R Samala
(74) *Attorney, Agent, or Firm* — Saul Ewing Arnstein & Lehr LLP; Kathryn Doyle; Domingos J. Silva

(57) ABSTRACT

The present disclosure provides imaging agents that are useful for the detection and evaluation of heart conditions, such as myocardial infarction. Upon activation, the imaging agents of the present disclosure may be detected using an ultrasound imaging device.

24 Claims, 16 Drawing Sheets

(56) References Cited

OTHER PUBLICATIONS

Dicker, et al., "Size distribution of microbubbles as a function of shell composition", Ultrasonics 53(7), Sep. 2013, 1363-1367 (Abstract Only).
Dierkes, et al., "Quantification of cell death due to ultrasound therapy with both traditional and nested microbubbles", Bubble Science Engineering and Technology, 2012. 4(2), Nov. 2012, 72-77 (Abstract Only).
Huang, et al., "Acoustically active liposomes for drug encapsulation and ultrasound-triggered release", Biochim Biophys Acta. 1665(1-2), Oct. 2004, 134-141.
Ibsen, et al., "A novel nested liposome drug delivery vehicle capable of ultrasound triggered release of its payload", Journal of Controlled Release, 155, 2011, 358-366.
Martz, et al., "Precision Manufacture of Phase-Change Perfluorocarbon Droplets Using Microfluidics", Ultrasound in Med. & Biol., vol. 37, No. 11, 2011, 1952-1957.
Mountford, et al., "Thermal Activation of Superheated Lipid-Coated Perfluorocarbon Drops", Langmuir, 31,, 2015, 4627-4634.
Nguyen, et al., "Acoustically active liposome-nanobubble complexes for enhanced ultrasonic imaging and ultrasound-triggered drug delivery", Wiley Interdiscip Rev Nanomed Nanobiotechnol. 6(3), May-Jun. 2014, 316-325 (Abstract Only).
Nguyen, et al., "Hydrophobic drug concentration affects the acoustic susceptibility of liposomes", Biochim Biophys Acta. 1850(4), Apr. 2015, 667-772 (Abstract Only).
Nguyen, et al., "Strategies for increasing acoustic susceptibility of liposomes for controlled drug delivery", Bubble Science Engineering and Technology 6, 2014, 25-31 (Abstract Only).
Porter, et al., "Targeted Transthoracic Acoustic Activation of Systemically Administered Nanodroplets to Detect Myocardial Perfusion Abnormalities", [downloaded from http://circimaging.abajournals.org/ on Jan. 16, 2018; DOI: 10.1161/CIRCIMAGING.115.003770].
Reznik, et al., "On the Acoustic Properties of Vaporized Submicron Perfluorocarbon Droplets", Ultrasound in Med. & Biol., vol. 40, No. 6,, 2014, 1379-1384.
Sheeran, et al., "Contrast-Enhanced Ultrasound Imaging and in Vivo Circulatory Kinetics With Low-Boiling-Point Nanoscale Phase-Change Perfluorocarbon Agents", Ultrasound in Med. & Biol., vol. 41, No. 3, 2015, 814-831.
Sheeran, et al., "Decafluorobutane as a Phase-Change Contrast Agent for Low-Energy Extravascular Ultrasonic Imaging", Ultrasound in Med. & Biol., vol. 37, No. 9, 2011, 1518-1530.
Sheeran, et al., "Design of ultrasonically-activatable nanoparticles using low boiling point perfluorocarbons", Biomaterials, 33,, 2012, 3262-3269.
Sheeran, et al., "Methods of Generating Submicrometer Phase-Shift Perfluorocarbon Droplets for Applications in Medical Ultrasonography", IEEE Transactions on Ultrasonics, Ferroelectrics, and Frequency Control, vol. 64, No. 1,, Jan. 2017, 252-263.
Small, et al., "Low-frequency ultrasound-induced transport across non-raft-forming ternary lipid bilayers", Langmuir. 28(40), Oct. 2012, 14364-14372 (Abstract Only).
Small, et al., "Ultrasound-induced transport across lipid bilayers: Influence of phase behavior", Colloids and Surfaces A: Physiochem. Eng. Aspects 390, 2011, 40-47 (Abstract Only).
Wallace, et al., "Inertial cavitation threshold of nested microbubbles", Ultrasonics 58, Apr. 2015, 67-74 (Abstract Only).
Wallace, et al., "Influence of nesting shell size on brightness longevity and resistance to ultrasound-induced dissolution during enhanced B-mode contrast imaging", Ultrasonics 54, 2014, 2099-2108 (Abstract Only).
Wallace, et al., "Ultrasound triggered drug delivery with liposomal nested microbubbles", Ultrasonics 63, Dec. 2015, 31-38 (Abstract Only).
Wrenn, et al., "Bursting bubbles and bilayers", Theranostics. 2012;2(12), 2012, 1140-1159.
Wrenn, et al., "Controlling Cavitation for Controlled Release", IEEE International Ultrasonics Symposium Proceedings, 2009, 104-107 (Abstract Only).
Wrenn, et al., "Microcapsules: Reverse Sonoporation and Long-lasting, Safe Contrast", Acoustical Imaging 31, 2012, 81-90 (Abstract Only).
Wrenn, et al., "Phospholipid-stabilized microbubbles: Influence of shell chemistry on cavitation threshold and binding to giant unilamellar vesicles", Applied Acoustics 70, 2009, 1313-1322.
Yoo, et al., "Impact of Encapsulation on in Vitro and in Vivo Performance of Volatile Nanoscale Phase-Shift Perfluorocarbon Droplets", Ultrasound in Med. & Biol., vol. 44, No. 8,, 2018, 1836-1852.
Zhou, et al., "Ultrasound-Mediated local drug and gene delivery using nanocarriers", Bio Med Res Int., 2014.

\* cited by examiner

- Nesting shell.
- Inner core.
- Liquid droplets.

FIG. 4A
FIG. 4B
FIG. 4C
FIG. 4D

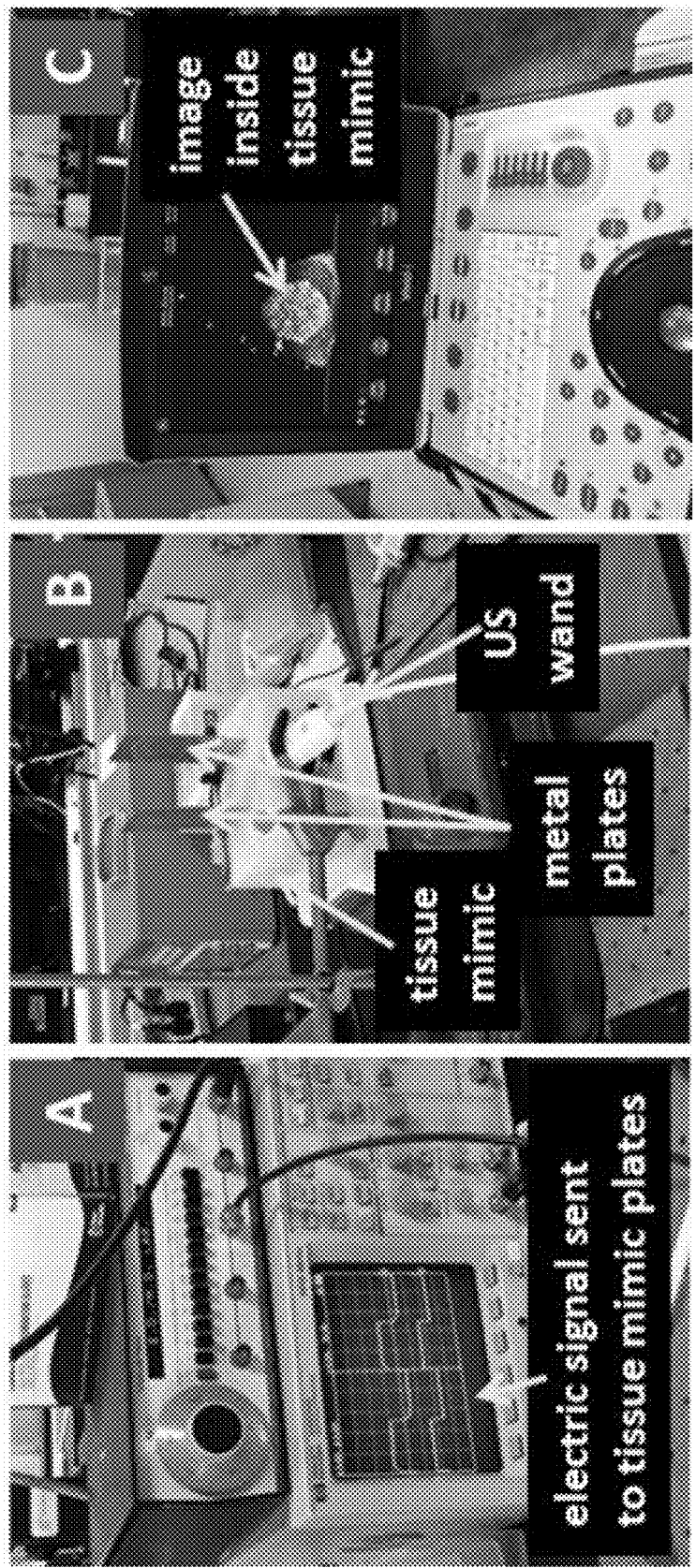

METHODS OF IMAGING AND DELIVERING THERAPEUTIC AGENTS

CROSS-REFERENCE TO RELATED APPLICATIONS

The present application is a continuation of, and claims priority to, U.S. patent application Ser. No. 17/204,561 filed Mar. 17, 2021, now allowed, which is a continuation of, and claims priority to, U.S. patent application Ser. No. 16/858,329 filed Apr. 24, 2020, now U.S. Pat. No. 10,980,898, which is continuation of, and claims priority to, U.S. patent application Ser. No. 16/029,335 filed Jul. 6, 2018, now abandoned, which claims priority under 35 U.S.C. § 119(e) to U.S. Provisional Application No. 62/529,700, filed Jul. 7, 2017, which is incorporated herein by reference in its entirety.

BACKGROUND OF THE INVENTION

Targeted drug delivery, or smart drug delivery, refers to methods of delivering a payload (such as a therapeutic agent, a diagnostic agent, and/or a therapeutic-diagnostic agent, also known as a "theranostic" agent) to a subject, such that the payload is preferentially (or exclusively) delivered to, or released in, certain parts of the subject's body relative to other parts. Targeted drug delivery has been attempted using nanoparticles, aiming to overcome downfalls of conventional systemic drug delivery. In principle, nanoparticles are loaded with an agent of interest, and are targeted to a certain body part that need treatment or diagnosis. In this way, use of nanoparticles avoid or minimize interaction of the agent with healthy tissue. Ideally, targeted drug delivery constructs should prolong and localize interaction of the payload agent with the tissue of interest. Further, targeted drug delivery should result in reduced administration frequency, more consistent effect, reduction of any side-effects, and reduced fluctuation in circulating levels of the agent.

Existing targeted drug delivery systems include liposomes, micelles, dendrimers, biodegradable particles, and artificial DNA nanostructures. However, the existing smart drug delivery constructs leave much to be desired, and there is active interest in identifying novel delivery constructs that respond to local physical characteristics of the tissue or organs to be treated and/or imaged.

Chest pain is the most common presenting complaint in a myriad of disorders ranging from life threatening acute myocardial infarction (AMI) to mild self-limiting disorders such as muscle strain. Chest pain and symptoms consistent with myocardial ischemia are common reasons for emergency department (ED) evaluation in the U.S., accounting for approximately 8-10% of the 119 million ED visits yearly. At least 6.5 million patients annually in the U.S. have to undergo physical examination for chest pain. In addition, over 8 million patients with chest pain are evaluated in the outpatient setting each year, posing a significant health burden. Health care professionals face the challenge of distinguishing life threatening cardiac causes of chest pain from non-cardiac etiologies, and this needs to be accomplished in a timely and efficient fashion. In the U.S. about 60% of ED patients with chest pain are further admitted to the hospital. However, despite such high admission rates, 3-4% of AMI patients are inadvertently discharged, while 40% of patients admitted to the critical care unit (CCU) with chest pain have all ischemic heart disease ruled out eventually.

The diagnosis of chest pains less than 12 hours in duration is an important challenge, because the majority of acute coronary syndrome (ACS)-related deaths occur within this period. Unfortunately, individual biochemical markers cannot effectively rule out myocardial infarction in the initial 12 hour period of chest pains. It is essential to identify all patients suffering from ACS, but it is important to control medical costs and minimize the occurrence of unnecessary investigations, cost-intensive inpatient care and resultant psychological stress. The current gold-standard for such evaluations involves 12-36 hours of continuous hospital monitoring, as well as use of radiation, expensive imaging equipment, and/or invasive catheter-based angiography.

There remains a need in the art for novel targeted drug delivery constructs, which can deliver a therapeutic, diagnostic, and/or theranostic agent to a tissue or organ of interest. Such constructs should be safe, easy and quick to use, and allow for accurate agent delivery. There also remains a need in the art for novel constructs that can be used to image a patient's cardiovascular system without requiring the use of radiation, invasive testing, and/or prolonged hospital stays. The present invention addresses and meets these needs.

BRIEF SUMMARY OF THE INVENTION

The invention provides construct comprising a liposome comprising a nesting shell. The invention further provides a method of selectively delivering a therapeutic, imaging and/or theranostic agent to a portion of a subject's body. The invention further provides a method of selectively imaging the portion of the subject's body.

In certain embodiments, the nesting shell encloses an inner compartment comprising an inner core liquid and at least one liquid droplet. In other embodiments, the at least one liquid droplet is insoluble in the inner core liquid.

In certain embodiments, the construct is more acoustically active in the presence of an electric field than in the absence of an electric field.

In certain embodiments, the at least one liquid droplet comprises an echogenic agent, which is devoid of acoustic activity when the construct is subjected to ultrasound in the absence of an electric field, and which has acoustic activity when the construct is subjected to ultrasound in the presence of an electric field.

In certain embodiments, the at least one liquid droplet comprises an echogenic agent, which has higher acoustic activity when the construct is subjected to ultrasound in the presence of an electric field as compared to in the absence of an electric field.

In certain embodiments, the inner compartment further comprises a therapeutic, diagnostic, and/or theranostic agent, which crosses the nesting shell at a higher rate in the presence of an electric field than in the absence of an electric field.

In certain embodiments, the at least one liquid droplet comprises a perfluorocarbon. In other embodiments, the at least one liquid droplet is selected from the group consisting of perfluoropropane, perfluorobutane, perfluoropentane, perfluorohexane, and any mixtures thereof.

In yet other embodiments, the at least one liquid droplet is coated with a coating that prevents contact of the inner core liquid with the at least one liquid droplet. In yet other embodiments, the coating prevents dissolution of the at least one liquid droplet within the inner core liquid. In yet other embodiments, in the absence of an electric field the coating prevents or minimizes at least one selected from the group consisting of aggregation, fusion, and coalescence of liquid droplets. In yet other embodiments, the coating comprises at least one selected from the group consisting of polysorbate 20, albumin, galactose, and polyethylene glycol.

In certain embodiments, the nesting shell comprises at least one selected from the group consisting of a phospholipid and a polymer. In other embodiments, the polymer is polymeric or self-assembled. In yet other embodiments, the at least one phospholipid comprises at least one phospholipid selected from the group consisting of saturated phospholipid, unsaturated phospholipid, phospholipid charged, and uncharged or zwitterion phospholipid. In yet other embodiments, the nesting shell comprises only uncharged or zwitterion phospholipids and/or polymers. In yet other embodiments, the nesting shell comprises at least two lipids, wherein one of the at least two lipids is saturated and the other lipid is unsaturated, and wherein one of the at least two lipids is charged and the other lipid is uncharged or zwitterion. In yet other embodiments, the two or more lipids are selected from the group consisting of stearoyl, oleoylphosphatidylglycerol (SOPG); di stearoylphosphatidylcholine (DSPC); stearoyl, oleoylphosphatidylcholine (SOPC); di stearoylphosphatidylglycerol (DSPG); cholesterol; and triolein. In yet other embodiments, the nesting shell comprises at least one lipid pair selected from the group consisting of: SOPG and SOPC; SOPG and DSPG; DSPC and SOPC; and DSPC and DSPG. In yet other embodiments, the at least one saturated lipid and at least one unsaturated lipid are: SOPG and DSPC; and/or SOPC and DSPG. In yet other embodiments, the nesting shell further comprises at least one pegylated lipid. In yet other embodiments, the nesting shell further comprises poly(vinyl alcohol). In yet other embodiments, the nesting shell comprises DSPC, SOPG, cholesterol and triolein. In yet other embodiments, the nesting shell comprises about 10-32.5 wt % DSPC, about 10-32.5 wt % SOPG, about 15-50 wt % cholesterol, and about 10-40 wt % triolein. In yet other embodiments, the nesting shell comprises DSPG, SOPC, cholesterol and triolein. In yet other embodiments, the nesting shell comprises about 10-32.5 wt % DSPG, about 10-32.5 wt % SOPC, about 15-50 wt % cholesterol, and about 10-40 wt % triolein.

In certain embodiments, the method comprises administering to the subject a construct of the invention, wherein the inner compartment comprises a therapeutic, imaging and/or theranostic agent. In other embodiments, if the portion of the subject's body produces a sufficient voltage gradient to render the nesting shell more permeable to the inner core liquid than in the absence of the voltage gradient, no further voltage gradient is applied to the portion of the subject's body. In yet other embodiments, if the portion of the subject's body does not produce a sufficient voltage gradient to render the nesting shell permeable to the inner core liquid, further voltage gradient is applied to the portion of the subject's body so as to render the nesting shell permeable to the inner core liquid.

In certain embodiments, the method comprises administering to the subject a construct of the invention, wherein the at least one liquid droplet comprises an echogenic agent. In other embodiments, the agent is devoid of acoustic activity when the construct is subjected to ultrasound in the absence of an electric field and has acoustic activity when the construct is subjected to ultrasound in the presence of an electric field. In yet other embodiments, the agent has higher acoustic activity when the construct is subjected to ultrasound in the presence of an electric field as compared to in the absence of an electric field. In other embodiments, the method comprises applying ultrasound radiation to the portion of the subject's body. In yet other embodiments, if the portion of the subject's body produces a sufficient voltage gradient to render the construct more acoustically active, no further voltage gradient is applied to the portion of the subject's bod. In yet other embodiments, if the portion of the subject's body does not produce a sufficient voltage gradient to render the construct more acoustically active than in the absence of the voltage gradient, further voltage gradient is applied to the portion of the subject's body so as to render the construct more acoustically active.

In certain embodiments, the portion of the subject's body is selected from the group consisting of heart, lung, liver, gallbladder, spleen, pancreas, kidneys, bladder, uterus, ovaries, eye, thyroid, parathyroid, scrotum, testicles, and abdominal cavity. In other embodiments, the portion of the subject's body is the heart or a section thereof.

In certain embodiments, the subject is a mammal. In other embodiments, the subject is a human.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 2A illustrates a non-limiting construct of the invention in the absence of voltage gradient. FIG. 2B illustrates a non-limiting construct of the invention in the presence of voltage gradient, as would arise for example upon depolarization of the heart. In this particular instance, the voltage gradient interacts with the nesting shell, causing the nesting shell to become more permeable to the aqueous interior and allowing for transport of material through or across (or both) the nesting shell.

FIG. 3A depicts a dual-activated construct subjected only to ultrasound. Without a voltage gradient, the nesting shell has low permeability (or none at all) to the aqueous interior. In certain embodiments, these conditions prevent vaporization of the contrast agent droplets within. In other embodiments, ultrasound by itself does not significantly activate or detect the voltage-activated construct. FIG. 3B depicts a dual-activated construct subjected to both ultrasound and a voltage gradient. The voltage gradient (electric field) causes the nesting shell to become more permeable to the aqueous interior. In certain embodiments, at least partial leakage of the aqueous interior allows for vaporization of the contrast agent droplets. In other embodiments, changes in the nesting shell due to the voltage gradient allow for increased acoustic activity of the construct.

FIGS. 4A-4D are non-limiting images demonstrating constructs of the invention being used in vitro in the presence of continuous, constant ultrasound of 0.28 MI (MI is defined as the Peak Negative Pressure, in MPa, divided by the square root of the ultrasound frequency, in MHz), 2.0/4.0 MHz. FIG. 4A is an image obtained before the construct was injected into the test chamber. FIG. 4B is an image obtained after 2 mL of the construct had been injected into the test chamber, in the absence of an applied voltage. FIG. 4C is an image of the test chamber with the construct in the presence of both ultrasound and an electric field of 1.25 V/cm, showing a slight visual difference in the brightness of the contrast as compared to FIG. 4B. FIG. 4D is an image of the test chamber with the construct in the presence of both ultrasound and an electric field of 3.25 V/cm. FIG. 4D shows greater acoustic activity than FIGS. 4B-4C, indicating that the construct is sensitive to the applied electric field.

FIGS. 5A-5C are images of the in vitro testing apparatus used to derive the images in FIGS. 4A-4D, meant to mimic clinical imaging of a heart. An electric signal programmed by a function generator (FIG. 5A) is sent to metal plates of a tissue mimic (FIG. 5B), coupled to a clinical ultrasound device (FIG. 5C).

FIG. 6A was acquired prior to injection. FIG. 6B was acquired after injection of voltage-activated construct; specifically, the formulation included 50 vol % PFP droplets coated with a monolayer of polysorbate 20 (5 vol % PFP, 0.1 vol % PS20, the balance water) and 50 vol % PBS nested with a bilayer comprising 22.5 wt % DSPG, 22.5 wt % SOPC, 25% cholesterol, 30 wt % triolein and suspended in water containing low molecular weight PVA. Comparison of FIGS. 6A-6B shows echogenic enhancement of the myocardium in FIG. 6B.

FIG. 7A was acquired prior to injection. FIG. 7B was acquired after injection of voltage-activated agents. Comparison of FIGS. 7A-7B shows echogenic enhancement of the myocardium in FIG. 7B.

FIG. 11A: Illustration of the fluorescence assay experimental set-up. The ultrasound transducer is placed into the top of the 3-D printed basin with its focal distance of 7.5 cm located within the cuvette at the height where the excitation light beam passes through the sample. Titanium electrodes are positioned 1 cm apart, and alligator clips are used to create varying sinusoidal potentials using a function generator; the electrode facing the emission monochromator has a hole to allow for passage of light to the detector. FIG. 11B: Photograph of the custom, 3-D printed housing inside the A-710 steady-state fluorescence spectrometer (Photon Technology International Inc., Birmingham, N.J.).

FIG. 12A: Photograph showing the ultrasound transducer of GE Vivid i in contact with the PVA cryogel tissue phantom. The two aluminum plates are inserted into the phantom 6 cm apart and span the sample region that has a diameter of 3 cm. FIG. 12B: Screenshot of an image generated using the GE Vivid i, showing the contrast-to-tissue ratio (CTR) methodology. Both regions chosen for brightness analysis are approximately 6 cm away from where the transducer couples to the phantom. The sample "contrast" (C of CTR) section is shown within the 3-cm circular sample cavity, while the "tissue" (T of CTR) section is outside the sample cavity.

DETAILED DESCRIPTION OF THE INVENTION

Figure 1:
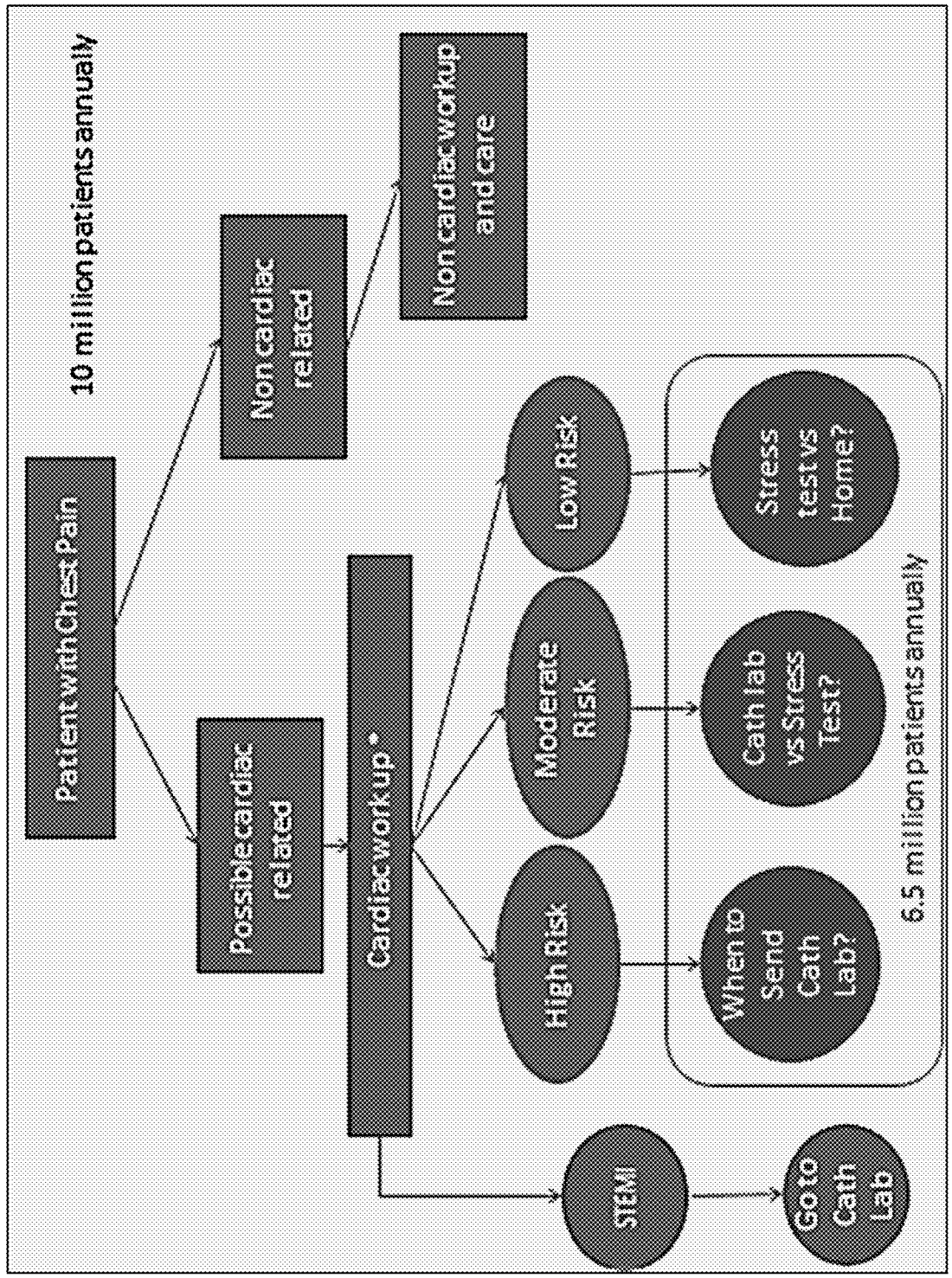
FIG. 1 is an algorithm chart detailing standard procedures in the art for diagnosing a patient with chest pain. In certain embodiments, the compositions and methods of the invention can be used to evaluate patients falling within the highlighted segment.
Figure 2A:
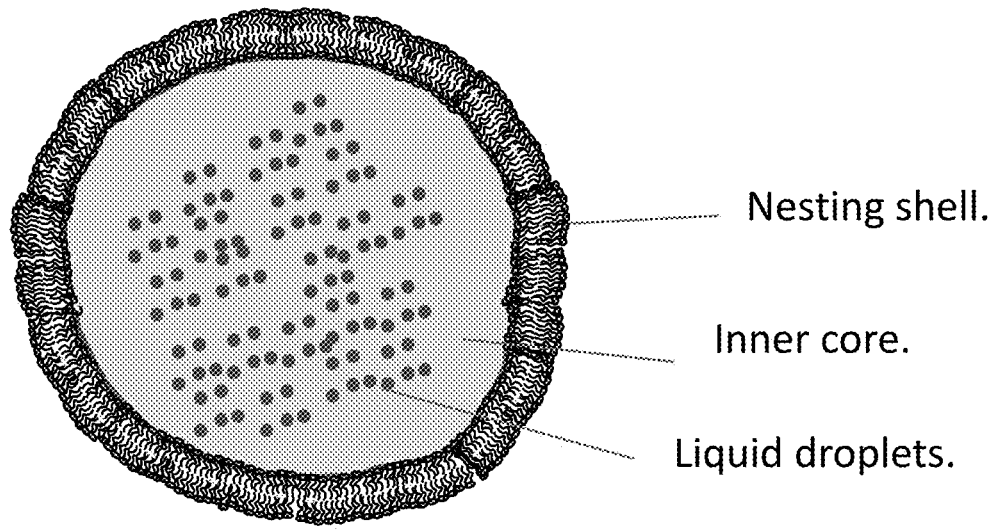
FIGS. 2A-2B are cartoon diagrams illustrating, in a non-limiting manner, voltage-activated theranostic constructs of the invention.
Figure 2B:
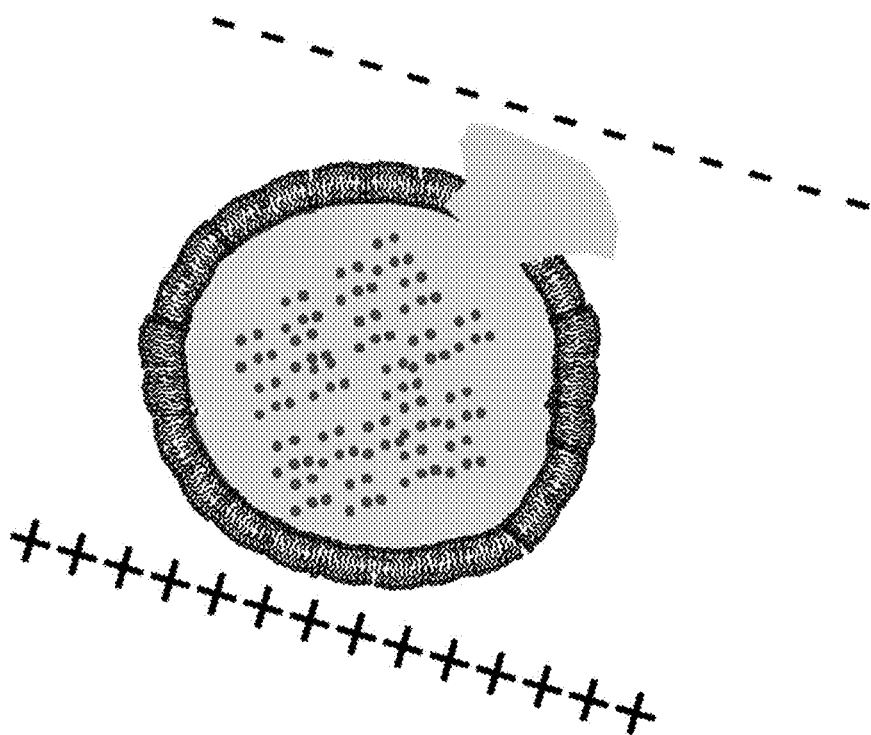
Figure 3A:
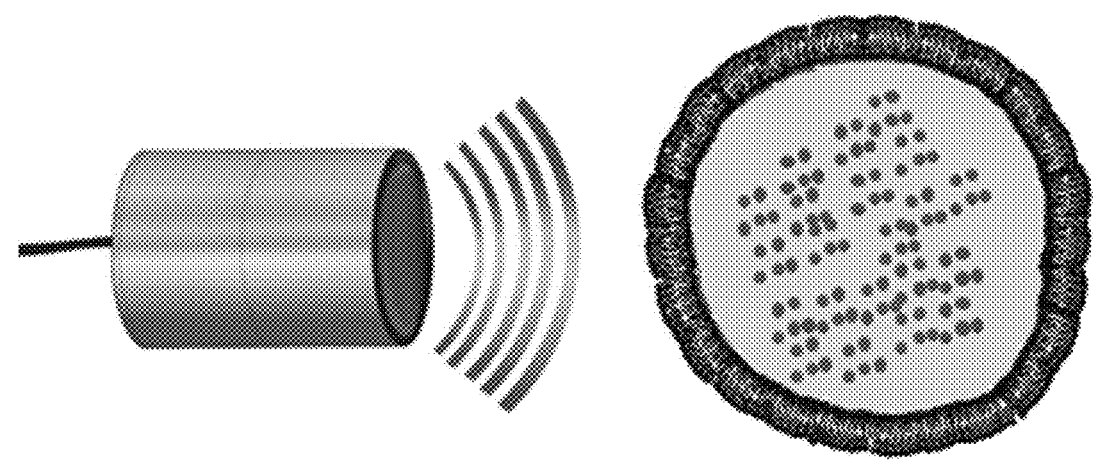
FIGS. 3A-3B are non-limiting cartoon diagrams illustrating certain dual voltage/ultrasound-activated theranostic constructs of the invention.
Figure 3B:
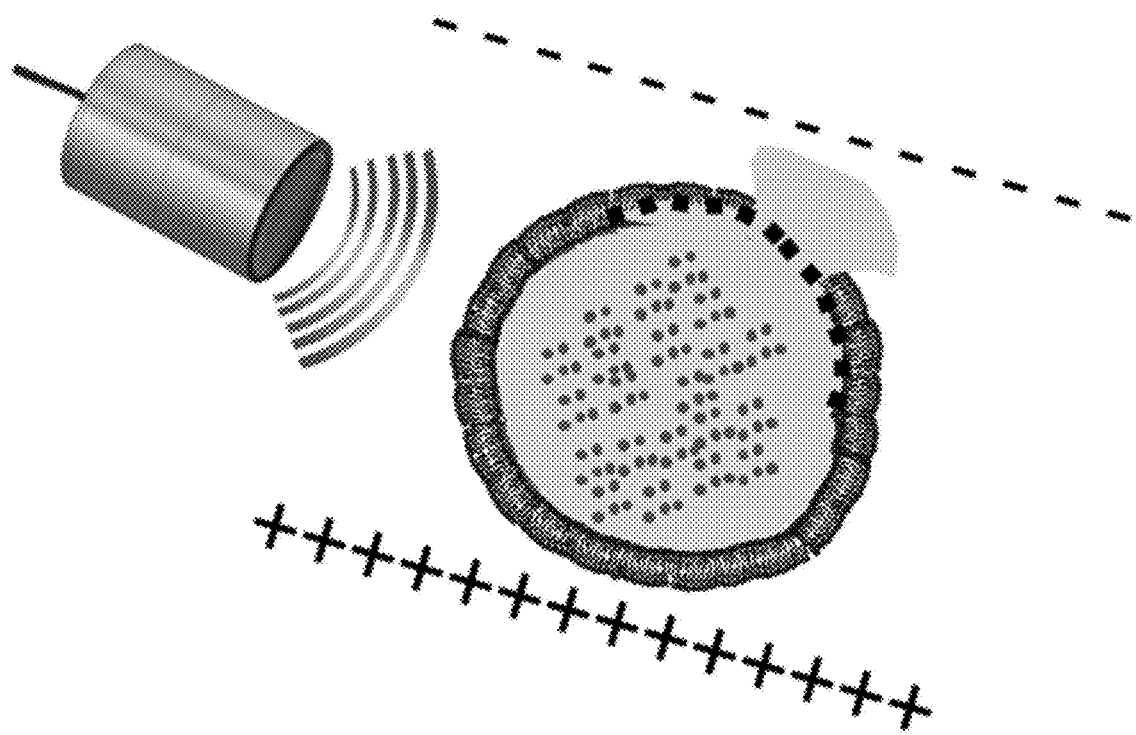

In one aspect, the present invention provides therapeutic, diagnostic, and/or theranostic constructs that can be used to deliver a specific payload to a tissue and/or organ of interest in a subject, and/or allow for specific imaging of a tissue and/or organ of interest in a subject.

In another aspect, the invention provides a construct comprising a liposome comprising a nesting shell, wherein the shell defines an inner compartment comprising an inner core liquid and liquid droplets, wherein the liquid droplets are insoluble in the inner core liquid. In certain non-limiting embodiments, the nesting shell is impermeable, or has lower permeability, to the inner core liquid in the absence of an electric field (voltage gradient). Upon applying an electric field, the nesting shell becomes more permeable to the inner core liquid than in the absence of an electric field (voltage gradient). In certain embodiments, the inner compartment further comprises a therapeutic, diagnostic and/or theranostic agent, wherein the nesting shell is more permeable to the agent in the presence of the electric field than in the absence thereof. In other embodiments, the liquid droplets comprise an echogenic agent, which is devoid of acoustic activity, or has low acoustic activity, when the construct is subjected to ultrasound in the absence of an electric field, but has acoustic activity, or has higher acoustic activity than in the absence of an electric field, when the construct is subjected to ultrasound in the presence of an electric field. In yet other embodiments, the construct is devoid of acoustic activity, or has low acoustic activity, when subjected to ultrasound in the absence of an electric field, but has acoustic activity, or has higher acoustic activity than in the absence of an electric field, when subjected to ultrasound in the presence of an electric field.

The invention should not be construed to be limited to the activation of the construct by an electric field. Indeed, the invention contemplates that the construct can be activated by any stimulus that causes the nesting shell to become more permeable to the inner core liquid and/or the therapeutic, diagnostic and/or theranostic agent, as compared to the absence of such stimulus, or by any stimulus that caused the construct to be more acoustically active. Non-limiting examples of stimuli contemplated within the invention include variation in pressure applied to the construct (for example, within the body, such as within a body compartment and/or a blood vessel) and/or binding of the construct to a cellular target, such as a receptor, enzyme, or any other biological molecule.

In certain embodiments, the liquid droplets comprise a perfluorocarbon. In other embodiments, the liquid droplets are coated with a coating. In yet other embodiments, the coating comprises polysorbate, surfactants, proteins, and/or polymers. In yet other embodiments, the coating prevents contact of the inner core liquid with the liquid droplets. In yet other embodiments, the coating prevents dissolution of the liquid droplets within the inner core liquid. In yet other embodiments, the coating prevents or minimizes aggregation, fusion, and/or coalescence of the liquid droplets.

In certain embodiments, the nesting shell comprises at least one phospholipid and/or a polymer. The polymer can be polymeric, such as but not limited to PLA, or self-assembled, such as but not limited to di-block, tri-block, and/or amphiphilic copolymers.

In certain embodiments, the at least one phospholipid comprises saturated, unsaturated, charged, and/or uncharged or zwitterion phospholipids. In other embodiments, the nesting shells comprises only uncharged or zwitterion phospholipids and/or polymers.

In certain embodiments, the nesting shell further comprises cholesterol. In other embodiments, the nesting shell further comprises a triglyceride, such as but not limited to triolein. In yet other embodiments, at least one lipid in the nesting shell is pegylated. In yet other embodiments, the nesting shell comprises poly(vinyl alcohol).

In certain embodiments, the inner core liquid comprises water. In other embodiments, the inner core liquid comprises a salt. In other embodiments, the inner core liquid comprises oil.

Without wishing to be limited by any theory, applying a voltage gradient (electric field) across the nesting shell causes a perturbation of at least a portion of the molecules within the nesting shell, so as to produce a reorientation and/or relocation of these molecules, and/or a concomitant change in microstructure of the nesting shell. In certain non-limiting embodiments, the perturbation of at least a portion of the molecules causes the entire nested structure, and/or any structures nested within, to become more acoustically active than in the absence of the voltage gradient. In certain non-limiting embodiments, the perturbation of at least a portion of the molecules causes a change in shell shape, thus producing enhanced acoustic scattering. In other non-limiting embodiments, the perturbation of at least a portion of the molecules causes deformation in the shell, allowing for at least partial vaporization of the nested droplets. In yet other non-limiting embodiments, the perturbation of at least a portion of the molecules causes the nesting shell to become "leaky" (i.e., at least partially permeable to components within the inner compartment). Once the nesting shell becomes "leaky," the construct is activated, and can deliver any existing payload to the tissue or organ of interest. In certain embodiments, the activated construct is combined with ultrasound to enable imaging of myocardial perfusion (see non-limiting illustrations in FIGS. 6A-6B and 7A-7B).

In certain embodiments, the constructs of the invention can be used to selectively image a portion of a subject's body. In other embodiments, the invention provides a "dual-activated" ultrasound construct, which becomes ultrasound active only when exposed simultaneously to ultrasound irradiation (and/or body temperature) and a voltage gradient. In certain embodiments, the construct of the invention can provide enhanced ultrasound contrast not only between blood vessels and tissue, but also between different regions of blood vessels (including arteries, arterioles, capillaries, venules, and veins). Such feature is suited to detect perfusion of the heart, and thus can provide a test for determining whether a subject is having or is prone to having a heart attack. Without wishing to be limited by any theory, the imaging construct of the invention comprises, inside the aqueous core of a liposome, an emulsion of coated, liquid droplets that have the potential to transition into gaseous microbubbles only if the liposome permits at least partial phase transition (and concomitant expansion) of the droplet into a gas bubble. In the presence of body temperature and/or an ultrasound field of a sufficient magnitude, but in the absence of a voltage gradient, the liposome does not permit transition of the liquid droplets into microbubbles. If ultrasound of sufficient magnitude is applied, or the construct is exposed to body temperature, while (and where) the liposomes are subjected to a voltage gradient of sufficient magnitude, then the liposomes permit transition of the liquid droplets into microbubbles, and the agent becomes acoustically active (that is, detectable with ultrasound). In certain non-limiting embodiments, at least partial vaporization takes place when the voltage gradients causes the shell shape to change, and/or causes deformation in the shell, and/or causes the nesting shell to become "leaky." Without wishing to be limited by any theory, the voltage gradient causes changes in the liposome, and/or any structures within, that result in enhanced acoustic scattering.

Without wishing to be limited by any theory, application of a voltage gradient to the construct of the invention causes a change in nature and/or structure of the nesting shell, which results in enhanced acoustic activity. In certain embodiments, the application of a voltage gradient results in enhanced acoustic scattering. In other embodiments, the application of a voltage gradient allows for transition of the liquid droplets into microbubbles. In certain embodiments, application of a voltage gradient to the construct of the invention alters permeability of the nesting shell to compounds such as water and/or salts. In other embodiments, a voltage gradient of sufficient magnitude causes charged lipids in the nesting shell, which are entropically distributed within the nesting shell in the absence of the voltage gradient, to rearrange within the liposome bilayer. This produces a change in permeability of the nesting shell to compounds such as water and/or salts and/or payload agents.

In certain embodiments, the methods of the invention comprise administering to the subject a construct of the invention, which is "activated" once the construct is exposed to a certain voltage gradient. In certain embodiments, activation of the construct of the invention comprises release of at least one active agent from the construct of the invention within the subject. In other embodiments, activation of the construct of the invention comprises ability to physically and/or chemically detect the activated construct of the invention, as compared to the non-activated construct, within the subject. The voltage gradient can be applied to the subject as needed, or can be generated within the subject as part of the subject's metabolism (such as by the portion of the subject's body being imaged).

In certain embodiments, the construct of the invention can be used for perfusion imaging of cardiac tissue. In other embodiments, the voltage gradients within the capillaries of cardiac muscle are of sufficient magnitude to activate the agent, whereas the voltage gradients within the chambers (ventricles, atria) of the heart are not. Thus, when ultrasound is applied, the agent becomes active only in the capillary regions and vasculature, thus enabling one to distinguish (using ultrasound) the flow of blood within the vasculature structures that exist in the myocardium from blood within the chambers of the heart. In certain embodiments, the construct of the invention activates in the presence of ultrasound only within electrically viable living, depolarizing tissue; the construct of the invention does not illuminate areas of myocardium that can be perfused but are electrically nascent or dead, as in ischemic or scarred myocardium. Identification of such areas of ischemia or scar are an essential part of evaluating myocardial perfusion. In certain embodiments, the construct of the invention can be coupled with vasodilator stress protocols, including pharmacological or exercise stress, to evaluate and visualize dynamic changes in the way the viable tissue is able to activate the agent.

In certain embodiments, a construct of the invention that has reaction and activation times comparable to the time taken for local tissue voltage changes as the depolarization wave moves through the heart muscle allows for visualization of actual depolarization wave through the tissue in real time by ultrasound. Visualization of the actual depolarization wave through the tissue shows areas of muscle that are abnormally depolarizing prematurely by reentrant circuits, accessary pathways or focal premature depolarizations, and facilitates non-invasive electrophysiological testing to localize areas of electrical anomaly that may be ameliorable to therapy, such as ablation, or that may benefit from specific pacing interventions, including guiding pacemaker resynchronization therapy.

In certain embodiments, a construct of the invention is clinically useful in assessing blood flow through vessels, tissue perfusion, and electrophysiological activity in peripheral vasculature, such as in the extremities and head. The construct can be activated using an "electrical activator" in the form of a band, cuff, pad, electrode or needle tip that is readily applied to the limb or neck. This activator creates an electrical gradient sufficient for activation of the agent.

Thus, the constructs of the invention can be used to evaluate and treat patients with chest pain and to help study electrophysiological patterns and abnormalities (arrhythmias and depolarization abnormalities). The constructs of the invention, in combination with readily available clinical ultrasound devices, allow for rapid, accurate, and relatively inexpensive determination of whether a patient is having a heart attack (a reduction of blood flow in certain regions of the heart), as well as demonstrate areas of myocardium that may be dead or ischemic. Further, the constructs of the invention can provide real time visualization of the actual depolarization wave as it passes through the myocardium, demonstrating areas of abnormal activation or arrhythmia patterns. The constructs of the invention can be used as a screening tool in both acute/urgent care and ambulatory settings. The constructs of the invention can further be used in the cardiac laboratories (catheterization, electrophysiology, and so forth) for direct myocardial perfusion assessment and/or electrophysiological mapping peri-procedurally. The constructs of the invention can further be used as a screening tool and peri-procecurally for vascular and neurological surgery.

In certain embodiments, the constructs of the invention comprise at least one liposome having a membrane, wherein the liposome encapsulates an aqueous core and at least one liquid droplet, which in certain embodiments comprises at least one ultrasound active compound, such as a perfluorocarbon.

DEFINITIONS

As used herein, each of the following terms has the meaning associated with it in this section. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in ultrasound imaging, animal testing and lipid chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the terms "effective amount" or "therapeutically effective amount" or "pharmaceutically effective amount" of a compound, composition, or construct are used interchangeably to refer to the amount of the compound, composition, or construct that is sufficient to provide a beneficial effect to the subject to which the compound is administered.

As used herein, an "instructional material" includes a publication, a recording, a diagram, or any other medium of expression, which can be used to communicate the usefulness of the compound and/or composition of the invention in the kit for carrying out the methods recited herein. The instructional material of the kit of the invention may, for example, be affixed to a container, which contains the chemical compound and/or composition of the invention or be shipped together with a container, which contains the chemical composition and/or composition. Alternatively, the instructional material may be shipped separately from the container with the intention that the instructional material and the compound be used cooperatively by the recipient.

As used herein, the term "nesting shell" refers to a shell (or membrane) that is capable of encapsulating an inner core, such that under certain experimental conditions the inner core is not capable of crossing the nesting shell, or the inner core has a lower rate of crossing the nesting shell as compared to other experimental conditions. Experimental conditions contemplated within the invention include, but are not limited to, electric field, ultrasound, pressure, temperature, flow stress, and the like.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N methylglucamine) and procaine. All of these salts may be prepared from the corresponding compound by reacting, for example, the appropriate acid or base with the compound.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

A "therapeutic" treatment is a treatment administered to a subject who exhibits signs of pathology for the purpose of diminishing or eliminating those signs.

"Treating," as used herein, means reducing the frequency with which symptoms are experienced by a patient or subject, or administering an agent or compound to reduce the severity with which symptoms are experienced by a patient or subject. An appropriate therapeutic amount in any individual case may be determined by one of ordinary skill in the art using routine experimentation.

As used herein, the term "triolein" refers to 2,3-bis[[(Z)-octadec-9-enoyl]oxy]propyl (Z)-octadec-9-enoate, or a slat or solvate thereof.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: ACS, acute coronary syndrome; AMI, acute myocardial infarction; DSPC, di stearoylphosphatidylcholine; DSPG, distearoylphosphatidylglycerol; PCA, phase-change agent; PFC, perfluorocarbon; PFP, perfluoropentane; PVA, polyvinylic acid; SOPC, stearoyl, oleoylphosphatidylcholine; SOPG, stearoyl, oleoylphosphatidylglycerol.

Compositions

The invention provides liposomal constructs that can be used in the drug delivery methods and/or imaging methods of the invention. In certain embodiments, the constructs of the invention comprise at least one liposome having a membrane (nesting shell), wherein the nesting shell encapsulates an aqueous core liquid and at least one liquid droplet, which in certain embodiments comprises at least one ultrasound active compound, such as a perfluorocarbon.

In certain embodiments, the nesting shell comprises cholesterol. In other embodiments, the nesting shell comprises triolein. In yet other embodiments, the nesting shell further comprises at least one saturated lipid and at least one unsaturated lipid; wherein one of the lipids is charged and the other lipid is uncharged or zwitterion.

In certain embodiments, the nesting shell comprises at least one lipid selected from the group consisting of SOPG and DSPG. In other embodiments, the nesting shell comprises at least one lipid selected from the group consisting of SOPC and DSPC. In yet other embodiments, the nesting shell comprises at least one lipid pair selected from the group consisting of: SOPG and SOPC; SOPG and DSPG; DSPC and SOPC; and DSPC and DSPG.

In certain embodiments, the liquid droplet comprises at least one perfluorinated ultrasound active compound. In other embodiments, the liquid droplet comprises perfluoropropane (C3). In yet other embodiments, the liquid droplet comprises perfluorobutane (C4). In other embodiments, the liquid droplet comprises perfluoropentane (C5). In other embodiments, the liquid droplet comprises perfluorohexane (C6). In other embodiments, the liquid droplet comprises sulfur hexafluoride. In yet other embodiments, the liquid droplet comprises about 5% (volume) at least one perfluorinated ultrasound active compound, such as for example C3, C4, C5, and/or C6.

In certain embodiments, the liquid droplet comprises a gaseous compound, which is gaseous under room temperature and pressure, but is liquid when formulated within the liquid droplet (such as, for example, by application of elevated pressure to the gaseous compound, by constraint of the gaseous compound within the coating, and/or dissolution within another liquid compound). In other embodiments, the liquefied gaseous compound becomes at least partially gaseous when the nesting shell is activated by a stimulus contemplated herein.

In certain embodiments, the droplet comprises dissolved gases, such as but not limited to $N_2$, $O_2$, $CO_2$, helium, neon, argon, krypton, xenon, and the like.

In certain embodiments, the droplet comprises particulate matter, such as but not limited to silica particles, gold particles, and/or magnetite particles. In other embodiments, the particulate matter ranges from about 1 nm diameter to about 100 nm diameter.

In certain embodiments, the liquid droplet comprises a coating comprising at least one selected from the group consisting of polysorbate 20, albumin, galactose, and polyethylene glycol. In other embodiments, the liquid droplet coating comprises polysorbate 20. In yet other embodiments, the liquid droplet comprises about 0.1% vol/vol polysorbate 20.

In certain embodiments, the nesting shell comprises SOPG, DSPC, cholesterol and triolein. In other embodiments, the nesting shell comprises about 22.5 wt % DSPC, about 22.5 wt % SOPG, about 25 wt % cholesterol and about 30 wt % triolein. In other embodiments, the nesting shell comprises about 20 wt % DSPC, about 20 wt % SOPG, about 40 wt % cholesterol and about 20 wt % triolein. In yet other embodiments, the nesting shell comprises about 20-22.5 wt % DSPC, about 20-22.5 wt % SOPG, about 25-40 wt % cholesterol, and about 20-30 wt % triolein. In yet other embodiments, the nesting shell comprises about 17.5-25 wt % DSPC, about 17.5-25 wt % SOPG, about 22.5-42.5 wt % cholesterol, and about 17.5-32.5 wt % triolein. In yet other embodiments, the nesting shell comprises about 15-27.5 wt % DSPC, about 15-27.5 wt % SOPG, about 20-45 wt % cholesterol, and about 15-35 wt % triolein. In yet other embodiments, the nesting shell comprises about 12.5-30 wt % DSPC, about 12.5-30 wt % SOPG, about 17.5-47.5 wt % cholesterol, and about 12.5-37.5 wt % triolein. In yet other embodiments, the nesting shell comprises about 10-32.5 wt % DSPC, about 10-32.5 wt % SOPG, about 15-50 wt % cholesterol, and about 10-40 wt % triolein.

In certain embodiments, the nesting shell comprises DSPG, SOPC, cholesterol and triolein. In other embodiments, the nesting shell comprises about 22.5 wt % DSPG, about 22.5 wt % SOPC, about 25 wt % cholesterol and about 30 wt % triolein. In other embodiments, the nesting shell comprises about 20 wt % DSPG, about 20 wt % SOPC, about 40 wt % cholesterol and about 20 wt % triolein. In yet other embodiments, the nesting shell comprises about 20-22.5 wt % DSPG, about 20-22.5 wt % SOPC, about 25-40 wt % cholesterol and about 20-30 wt % triolein. In yet other embodiments, the nesting shell comprises about 17.5-25 wt % DSPG, about 17.5-25 wt % SOPC, about 22.5-42.5 wt % cholesterol, and about 17.5-32.5 wt % triolein. In yet other embodiments, the nesting shell comprises about 15-27.5 wt % DSPG, about 15-27.5 wt % SOPC, about 20-45 wt % cholesterol, and about 15-35 wt % triolein. In yet other embodiments, the nesting shell comprises about 12.5-30 wt % DSPG, about 12.5-30 wt % SOPC, about 17.5-47.5 wt % cholesterol, and about 12.5-37.5 wt % triolein. In yet other embodiments, the nesting shell comprises about 10-32.5 wt % DSPG, about 10-32.5 wt % SOPC, about 15-50 wt % cholesterol, and about 10-40 wt % triolein.

In certain embodiments, the nesting shell comprises about 22.5 wt % DSPC. In other embodiments, the nesting shell comprises about 22.5 wt % SOPG. In yet other embodiments, the nesting shell comprises about 25 wt % cholesterol. In yet other embodiments, the nesting shell comprises about 30 wt % triolein. In yet other embodiments, the nesting shell comprises about 20 wt % DSPC. In yet other embodiments, the nesting shell comprises about 20 wt % SOPG. In yet other embodiments, the nesting shell comprises about 40 wt % cholesterol. In yet other embodiments, the nesting shell comprises about 20 wt % triolein. In yet other embodiments, the nesting shell comprises about 20-22.5 wt % DSPC. In yet other embodiments, the nesting shell comprises about 20-22.5 wt % SOPG. In yet other embodiments, the nesting shell comprises about 25-40 wt % cholesterol. In yet other embodiments, the nesting shell comprises about 20-30 wt % triolein. In yet other embodiments, the nesting shell comprises about 17.5-25 wt % DSPC. In yet other embodiments, the nesting shell comprises about 17.5-25 wt % SOPG. In yet other embodiments, the nesting shell comprises about 22.5-42.5 wt % cholesterol. In yet other embodiments, the nesting shell comprises about 17.5-32.5 wt % triolein. In yet other embodiments, the nesting shell comprises about 15-27.5 wt % DSPC. In yet other embodiments, the nesting shell comprises about 15-27.5 wt % SOPG. In yet other embodiments, the nesting shell comprises about 20-45 wt % cholesterol. In yet other embodiments, the nesting shell comprises about 15-35 wt % triolein. In yet other embodiments, the nesting shell comprises about 12.5-30 wt % DSPC. In yet other embodiments, the nesting shell comprises about 12.5-30 wt % SOPG. In yet other embodiments, the nesting shell comprises about 17.5-47.5 wt % cholesterol. In yet other embodiments, the nesting shell comprises about 12.5-37.5 wt % triolein. In yet other embodiments, the nesting shell comprises about 10-32.5 wt % DSPC. In yet other embodiments, the nesting shell comprises about 10-32.5 wt % SOPG. In yet other embodiments, the nesting shell comprises about 15-50 wt % cholesterol. In yet other embodiments, the nesting shell comprises about 10-40 wt % triolein. In yet other embodiments, the nesting shell comprises about 22.5 wt % DSPG. In yet other embodiments, the nesting shell comprises about 22.5 wt % SOPC. In yet other embodiments, the nesting shell comprises about 25 wt % cholesterol. In yet other embodiments, the nesting shell comprises about 30 wt % triolein. In yet other embodiments, the nesting shell comprises about 20 wt % DSPG. In yet other embodiments, the nesting shell comprises about 20 wt % SOPC. In yet other embodiments, the nesting shell comprises about 40 wt % cholesterol. In yet other embodiments, the nesting shell comprises about 20 wt % triolein. In yet other embodiments, the nesting shell comprises about 20-22.5 wt % DSPG. In yet other embodiments, the nesting shell comprises about 20-22.5 wt % SOPC. In yet other embodiments, the nesting shell comprises about 25-40 wt % cholesterol. In yet other embodiments, the nesting shell comprises about 20-30 wt % triolein. In yet other embodiments, the nesting shell comprises about 17.5-25 wt % DSPG. In yet other embodiments, the nesting shell comprises about 17.5-25 wt % SOPC. In yet other embodiments, the nesting shell comprises about 22.5-42.5 wt % cholesterol. In yet other embodiments, the nesting shell comprises about 17.5-32.5 wt % triolein. In yet other embodiments, the nesting shell comprises about 15-27.5 wt % DSPG. In yet other embodiments, the nesting shell comprises about 15-27.5 wt % SOPC. In yet other embodiments, the nesting shell comprises about 20-45 wt % cholesterol. In yet other embodiments, the nesting shell comprises about 15-35 wt % triolein. In yet other embodiments, the nesting shell comprises about 12.5-30 wt % DSPG. In yet other embodiments, the nesting shell comprises about 12.5-30 wt % SOPC. In yet other embodiments, the nesting shell comprises about 17.5-47.5 wt % cholesterol. In yet other embodiments, the nesting shell comprises about 12.5-37.5 wt % triolein. In yet other embodiments, the nesting shell comprises about 10-32.5 wt % DSPG. In yet other embodiments, the nesting shell comprises about 10-32.5 wt % SOPC. In yet other embodiments, the nesting shell comprises about 15-50 wt % cholesterol. In yet other embodiments, the nesting shell comprises about 10-40 wt % triolein.

In certain embodiments, the construct comprises: liquid droplets comprising about 5% vol/vol perfluoropentane and about 0.1% vol/vol polysorbate 20; and a nesting shell comprising about 22.5 wt % DSPC, about 22.5 wt % SOPG, about 25 wt % cholesterol, and about 30 wt % triolein.

In other embodiments, the construct comprises: liquid droplets comprising about 5% vol/vol perfluoropentane and about 0.1% vol/vol polysorbate 20; and a nesting shell comprising about 22.5 wt % DSPG, about 22.5 wt % SOPC, about 25 wt % cholesterol, and about 30 wt % triolein.

In certain embodiments, the construct is suspended in an aqueous solution comprising low molecular weight poly (vinyl alcohol).

In certain embodiments, the constructs of the invention are formulated in admixtures with conventional excipients, i.e., pharmaceutically acceptable organic or inorganic carrier substances suitable for parenteral, intravenous, intra-arterial, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, and/or coloring substances and the like. They may also be combined where desired with other active agents.

In certain embodiments, the construct further comprises an additional outer membrane that encapsulates the nesting shell. In certain embodiments, the outer membrane comprises a lipid bilayer. In other embodiments, the outer membrane protects the nesting shell from degradation under biological conditions.

Kits

The invention further provides a kit comprising at least one composition or construct of the invention, and an instruction manual reciting a method of diagnosing and/or treating using the at least one composition or construct of the invention. In certain embodiments, the kit further comprises an ultrasound imaging device and/or payload agent. In other embodiments, the kit further comprises a device for applying a voltage gradient.

Methods

The invention provides methods of delivery a payload agent (which can be a therapeutic, imaging, and/or theranostic agent) to a portion of a subject's body. In certain embodiments, the method comprises administering to the subject a construct of the invention, wherein the payload agent is released from the construct at a higher rate in the presence of a voltage gradient than in the absence of a voltage gradient. In other embodiments, the construct is more permeable to the payload agent in the presence of a voltage gradient than in the absence of a voltage gradient. If the portion of the body produces a sufficient voltage gradient to activate the construct, no further voltage gradient is applied to the portion of the subject's body. If the portion of the body does not produce a sufficient voltage gradient to activate the construct, further voltage gradient is applied to the portion of the subject's body so as to activate the construct.

The invention also provides methods of selectively imaging a portion of a subject's body using a "dual-activated" construct of the invention. In certain embodiments, the method comprises administering to the subject a construct of the invention, wherein the construct is ultrasound-inactive in the absence of both a voltage gradient and ultrasound irradiation. In other embodiments, the method comprises applying ultrasound irradiation to the portion of the subject's body. If the portion of the body produces a sufficient voltage gradient to activate the construct, no further voltage gradient is applied to the portion of the subject's body. If the portion of the body does not produce a sufficient voltage gradient to activate the construct, further voltage gradient is applied to the portion of the subject's body so as to activate the construct. In yet other embodiments, the method comprises imaging the portion of the subject's body.

In certain embodiments, the portion of the subject's body is imaged using ultrasound imaging.

In certain embodiments, the ultrasound contrast construct comprises a liposome having a nesting shell, wherein the nesting shell encapsulates an aqueous core liquid and at least one liquid particle encapsulating at least one ultrasound active compound. In other embodiments, the nesting shell of the liposome becomes at least partially permeable to the aqueous core liquid when subjected to a voltage gradient.

In certain embodiments, the at least one ultrasound active compound is any ultrasound active compound known in the art. In other embodiments, the at least one ultrasound active compound comprises perfluoropropane (C3). In yet other embodiments, the at least one ultrasound active compound comprises perfluorobutane (C4). In other embodiments, the at least one ultrasound active compound comprises perfluoropentane (C5). In other embodiments, the at least one ultrasound active compound comprises perfluorohexane (C6). In other embodiments, the at least one ultrasound active compound comprises sulfur hexafluoride. In yet other embodiments, the at least one ultrasound active compound is selected from the group consisting of perfluoropropane, perfluorobutane, perfluoropentane, and perfluorohexane. In yet other embodiments, the ultrasound active compound is perfluoropentane.

Without wishing to be limited by any theory, the activity of the at least one ultrasound active compound within the constructs of the invention can be influenced by the boiling point of the compound, the droplet size of the compound, the presence (or absence) of dissolved gases (such as, but not limited to, $O_2$, $N_2$, $CO_2$, and so forth) in the inner core liquid, and/or the presence (or absence) of particulate matter in the inner core liquid.

In certain embodiments, the liquid droplet comprises a gaseous compound, which is gaseous under room temperature and pressure, but is liquid when formulated within the liquid droplet (such as, for example, by application of elevated pressure to the gaseous compound, by constraint of the gaseous compound within the coating, and/or dissolution within another liquid compound). In other embodiments, the liquefied gaseous compound becomes at least partially gaseous when the nesting shell is activated by a stimulus contemplated herein.

In certain embodiments, the at least one liquid particle comprises a coating comprising at least one selected from the group consisting of polysorbate 20, albumin, galactose, and polyethylene glycol. In other embodiments, the coating comprises polysorbate 20.

In certain embodiments, the at least one liquid particle comprises perfluoropentane encapsulated within a monolayer of polysorbate 20.

In certain embodiments, the nesting shell comprises at least one lipid selected from the group consisting of SOPG and DSPG. In other embodiments, the nesting shell comprises at least one lipid selected from the group consisting of SOPC and DSPC. In yet other embodiments, the nesting shell comprises at least one lipid pair selected from the group consisting of: SOPG and SOPC; SOPG and DSPG; DSPC and SOPC; and DSPC and DSPG.

In certain embodiments, the nesting shell further comprises cholesterol. In other embodiments, the nesting shell further comprises triolein.

In certain embodiments, a voltage gradient is applied to the portion of the subject's body so as to activate the construct. In other embodiments, the voltage gradient applied does not cause significant electroporation. In yet other embodiments, the voltage gradient is equal to or less than about 10 V/cm. In yet other embodiments, the voltage gradient ranges from about 0.01 V/cm to about 10 V/cm. In yet other embodiments, the voltage gradient ranges from about 0.05 V/cm to about 10 V/cm. In yet other embodiments, the voltage gradient ranges from about 0.1 V/cm to about 10 V/cm. In yet other embodiments, the voltage gradient ranges from about 0.5 V/cm to about 10 V/cm.

In certain embodiments, the voltage range is equal to or higher than about 0.01 V/cm. In other embodiments, the voltage range is equal to or higher than about 0.02 V/cm. In yet other embodiments, the voltage range is equal to or higher than about 0.03 V/cm. In yet other embodiments, the voltage range is equal to or higher than about 0.04 V/cm. In yet other embodiments, the voltage range is equal to or higher than about 0.05 V/cm. In yet other embodiments, the voltage range is equal to or higher than about 0.06 V/cm. In yet other embodiments, the voltage range is equal to or higher than about 0.07 V/cm. In yet other embodiments, the voltage range is equal to or higher than about 0.08 V/cm. In yet other embodiments, the voltage range is equal to or higher than about 0.09 V/cm. In yet other embodiments, the voltage range is equal to or higher than about 0.1 V/cm. In yet other embodiments, the voltage range is equal to or higher than about 0.2 V/cm. In yet other embodiments, the voltage range is equal to or higher than about 0.3 V/cm. In yet other embodiments, the voltage range is equal to or higher than about 0.4 V/cm. In yet other embodiments, the voltage range is equal to or higher than about 0.5 V/cm. In yet other embodiments, the voltage range is equal to or higher than about 0.6 V/cm. In yet other embodiments, the voltage range is equal to or higher than about 0.7 V/cm. In yet other embodiments, the voltage range is equal to or higher than about 0.8 V/cm. In yet other embodiments, the voltage range is equal to or higher than about 0.9 V/cm. In yet other embodiments, the voltage range is equal to or higher than about 1.0 V/cm. In yet other embodiments, the voltage range is equal to or higher than about 1.2 V/cm. In yet other embodiments, the voltage range is equal to or higher than about 1.4 V/cm. In yet other embodiments, the voltage range is equal to or higher than about 1.6 V/cm. In yet other embodiments, the voltage range is equal to or higher than about 1.8 V/cm. In yet other embodiments, the voltage range is equal to or higher than about 2.0 V/cm. In yet other embodiments, the voltage range is equal to or higher than about 2.2 V/cm. In yet other embodiments, the voltage range is equal to or higher than about 2.4 V/cm. In yet other embodiments, the voltage range is equal to or higher than about 2.6 V/cm. In yet other embodiments, the voltage range is equal to or higher than about 2.8 V/cm. In yet other embodiments, the voltage range is equal to or higher than about 3.0 V/cm. In yet other embodiments, the voltage range is equal to or higher than about 3.2 V/cm. In yet other embodiments, the voltage range is equal to or higher than about 3.4 V/cm. In yet other embodiments, the voltage range is equal to or higher than about 3.6 V/cm. In yet other embodiments, the voltage range is equal to or higher than about 3.8 V/cm. In yet other embodiments, the voltage range is equal to or higher than about 4.0 V/cm. In yet other embodiments, the voltage range is equal to or higher than about 4.2 V/cm. In yet other embodiments, the voltage range is equal to or higher than about 4.4 V/cm. In yet other embodiments, the voltage range is equal to or higher than about 4.6 V/cm. In yet other embodiments, the voltage range is equal to or higher than about 4.8 V/cm. In yet other embodiments, the voltage range is equal to or higher than about 5.0 V/cm. In yet other embodiments, the voltage range is equal to or higher than about 5.2 V/cm. In yet other embodiments, the voltage range is equal to or higher than about 5.4 V/cm. In yet other embodiments, the voltage range is equal to or higher than about 5.6 V/cm. In yet other embodiments, the voltage range is equal to or higher than about 5.8 V/cm. In yet other embodiments, the voltage range is equal to or higher than about 6.0 V/cm. In yet other embodiments, the voltage range is equal to or higher than about 6.2 V/cm. In yet other embodiments, the voltage range is equal to or higher than about 6.2 V/cm. In yet other embodiments, the voltage range is equal to or higher than about 6.4 V/cm. In yet other embodiments, the voltage range is equal to or higher than about 6.6 V/cm. In yet other embodiments, the voltage range is equal to or higher than about 6.8 V/cm. In yet other embodiments, the voltage range is equal to or higher than about 7.0 V/cm. In yet other embodiments, the voltage range is equal to or higher than about 7.2 V/cm. In yet other embodiments, the voltage range is equal to or higher than about 7.4 V/cm. In yet other embodiments, the voltage range is equal to or higher than about 7.6 V/cm. In yet other embodiments, the voltage range is equal to or higher than about 7.8 V/cm. In yet other embodiments, the voltage range is equal to or higher than about 8.0 V/cm. In yet other embodiments, the voltage range is equal to or higher than about 8.2 V/cm. In yet other embodiments, the voltage range is equal to or higher than about 8.4 V/cm. In yet other embodiments, the voltage range is equal to or higher than about 8.6 V/cm. In yet other embodiments, the voltage range is equal to or higher than about 8.8 V/cm. In yet other embodiments, the voltage range is equal to or higher than about 9.0 V/cm. In yet other embodiments, the voltage range is equal to or higher than about 9.2 V/cm. In yet other embodiments, the voltage range is equal to or higher than about 9.4 V/cm. In yet other embodiments, the voltage range is equal to or higher than about 9.6 V/cm. In yet other embodiments, the voltage range is equal to or higher than about 9.8 V/cm. In yet other embodiments, the voltage range is equal to about 10 V/cm.

In certain embodiments, the voltage range is equal to about 0.01 V/cm. In other embodiments, the voltage range is equal to or lower than about 0.02 V/cm. In yet other embodiments, the voltage range is equal to or lower than about 0.03 V/cm. In yet other embodiments, the voltage range is equal to or lower than about 0.04 V/cm. In yet other embodiments, the voltage range is equal to or lower than about 0.05 V/cm. In yet other embodiments, the voltage range is equal to or lower than about 0.06 V/cm. In yet other embodiments, the voltage range is equal to or lower than about 0.07 V/cm. In yet other embodiments, the voltage range is equal to or lower than about 0.08 V/cm. In yet other embodiments, the voltage range is equal to or lower than about 0.09 V/cm. In yet other embodiments, the voltage range is equal to or lower than about 0.1 V/cm. In yet other embodiments, the voltage range is equal to or lower than about 0.2 V/cm. In yet other embodiments, the voltage range is equal to or lower than about 0.3 V/cm. In yet other embodiments, the voltage range is equal to or lower than about 0.4 V/cm. In yet other embodiments, the voltage range is equal to or lower than about 0.5 V/cm. In yet other embodiments, the voltage range is equal to or lower than about 0.6 V/cm. In yet other embodiments, the voltage range is equal to or lower than about 0.7 V/cm. In yet other embodiments, the voltage range is equal to or lower than about 0.8 V/cm. In yet other embodiments, the voltage range is equal to or lower than about 0.9 V/cm. In yet other embodiments, the voltage range is equal to or lower than about 1.0 V/cm. In yet other embodiments, the voltage range is equal to or lower than about 1.2 V/cm. In yet other embodiments, the voltage range is equal to or lower than about 1.4 V/cm. In yet other embodiments, the voltage range is equal to or lower than about 1.6 V/cm. In yet other embodiments, the voltage range is equal to or lower than about 1.8 V/cm. In yet other embodiments, the voltage range is equal to or lower than about 2.0 V/cm. In yet other embodiments, the voltage range is equal to or lower than about 2.2 V/cm. In yet other embodiments, the voltage range is equal to or lower than about 2.4 V/cm. In yet other embodiments, the voltage range is equal to or lower than about 2.6 V/cm. In yet other embodiments, the voltage range is equal to or lower than about 2.8 V/cm. In yet other embodiments, the voltage range is equal to or lower than about 3.0 V/cm. In yet other embodiments, the voltage range is equal to or lower than about 3.2 V/cm. In yet other embodiments, the voltage range is equal to or lower than about 3.4 V/cm. In yet other embodiments, the voltage range is equal to or lower than about 3.6 V/cm. In yet other embodiments, the voltage range is equal to or lower than about 3.8 V/cm. In yet other embodiments, the voltage range is equal to or lower than about 4.0 V/cm. In yet other embodiments, the voltage range is equal to or lower than about 4.2 V/cm. In yet other embodiments, the voltage range is equal to or lower than about 4.4 V/cm. In yet other embodiments, the voltage range is equal to or lower than about 4.6 V/cm. In yet other embodiments, the voltage range is equal to or lower than about 4.8 V/cm. In yet other embodiments, the voltage range is equal to or lower than about 5.0 V/cm. In yet other embodiments, the voltage range is equal to or lower than about 5.2 V/cm. In yet other embodiments, the voltage range is equal to or lower than about 5.4 V/cm. In yet other embodiments, the voltage range is equal to or lower than about 5.6 V/cm. In yet other embodiments, the voltage range is equal to or lower than about 5.8 V/cm. In yet other embodiments, the voltage range is equal to or lower than about 6.0 V/cm. In yet other embodiments, the voltage range is equal to or lower than about 6.2 V/cm. In yet other embodiments, the voltage range is equal to or lower than about 6.2 V/cm. In yet other embodiments, the voltage range is equal to or lower than about 6.4 V/cm. In yet other embodiments, the voltage range is equal to or lower than about 6.6 V/cm. In yet other embodiments, the voltage range is equal to or lower than about 6.8 V/cm. In yet other embodiments, the voltage range is equal to or lower than about 7.0 V/cm. In yet other embodiments, the voltage range is equal to or lower than about 7.2 V/cm. In yet other embodiments, the voltage range is equal to or lower than about 7.4 V/cm. In yet other embodiments, the voltage range is equal to or lower than about 7.6 V/cm. In yet other embodiments, the voltage range is equal to or lower than about 7.8 V/cm. In yet other embodiments, the voltage range is equal to or lower than about 8.0 V/cm. In yet other embodiments, the voltage range is equal to or lower than about 8.2 V/cm. In yet other embodiments, the voltage range is equal to or lower than about 8.4 V/cm. In yet other embodiments, the voltage range is equal to or lower than about 8.6 V/cm. In yet other embodiments, the voltage range is equal to or lower than about 8.8 V/cm. In yet other embodiments, the voltage range is equal to or lower than about 9.0 V/cm. In yet other embodiments, the voltage range is equal to or lower than about 9.2 V/cm. In yet other embodiments, the voltage range is equal to or lower than about 9.4 V/cm. In yet other embodiments, the voltage range is equal to or lower than about 9.6 V/cm. In yet other embodiments, the voltage range is equal to or lower than about 9.8 V/cm. In yet other embodiments, the voltage range is equal to or lower than about 10 V/cm.

In certain embodiments, the methods of the invention are used to image a portion of the subject's body selected from the group consisting of heart, lung, liver, gallbladder, spleen, pancreas, kidneys, bladder, uterus, ovaries, eye, thyroid, parathyroid, scrotum, testicles, and abdominal cavity. In other embodiments, the portion of the subject's body is the heart or a section thereof. In yet other embodiments, the portion of the subject's body is a ventricle of the subject's heart. In yet other embodiments, an external electrical field is applied to the portion of the subject's body, regardless of whether the portion of the subject's body inherently generates electrical activity.

In certain embodiments, the portion of the body produces a sufficient voltage gradient to activate the construct, wherein no further voltage gradient is applied to the portion of the subject's body. In certain embodiments, the portion of the body that produces a sufficient voltage gradient to activate the construct is the heart.

In certain embodiments, the portion of the subject's body is subjected to a single ultrasound irradiation frequency and/or intensity. In other embodiments, the portion of the subject's body is subjected to two or more different ultrasound irradiation frequencies and/or intensities. In certain embodiments, the ultrasound applied to the portion of the subject's body is equal to or less than 1.9, 1.8, 1.7, 1.6, 1.5, 1.4, 1.3, 1.2, 1.1, or 1.0.

In certain embodiments, the "dual-activated" construct is administered to the subject as part of a pharmaceutical composition, further comprising one or more excipients.

In certain embodiments, the "dual-activated" construct is administered to the subject through one or more methods selected from the group consisting of parenteral, intravenous, intra-arterial, and so forth, using for example injections and/or infusions.

In certain embodiments, the methods of the invention are non-invasive. In other embodiments, the methods of the invention do not comprise the use of ionizing radiation. In yet other embodiments, the methods of the invention allow for stronger ultrasound image contrast when compared to other methods common in the art. In yet other embodiments, the methods of the invention allow for a lower dosage of the "dual-activated" construct to attain comparable ultrasound image contrast when compared to other methods common in the art. In yet other embodiments, the methods of the invention allow for the assessment of micro-vascular perfusion. In certain embodiments, the subject is a mammal. In other embodiments, the subject is a human.

Administration/Dosage/Formulations

The regimen of administration may affect what constitutes an effective amount. The therapeutic formulations, compositions, and/or constructs may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such compound for the treatment of a disease or disorder contemplated in the invention.

In certain embodiments, the compositions or constructs of the invention are formulated using one or more pharmaceutically acceptable excipients or carriers. In other embodiments, the pharmaceutical compositions or constructs of the invention are formulated using one or more pharmaceutically acceptable excipients or of the invention comprise a therapeutically effective amount of a compound of the invention and a pharmaceutically acceptable carrier. In yet other embodiments, the compound of the invention is the only biologically active agent in the composition. In yet other embodiments, the compound of the invention is the only biologically active agent in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include, for example, intravenous or intra-arterial injection and/or infusion.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier.

The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: In Vitro Experiments Using "Dual-Activated" Contrast Agents

FIGS. 4A-4D illustrates an in vitro proof of concept experiment with cholesterol- and triolein-containing constructs. As compared to deionized water (FIG. 4A), which is essentially dark, the highest voltage gradient (3.33 V/cm, FIG. 4D), appears bright.

Example 2: In Vivo Experiments Using "Dual-Activated" Contrast Agents

Figure 6A:
FIGS. 6A-6B are in vivo images of the left ventricle of a rat heart (long axis view).
Figure 6B:
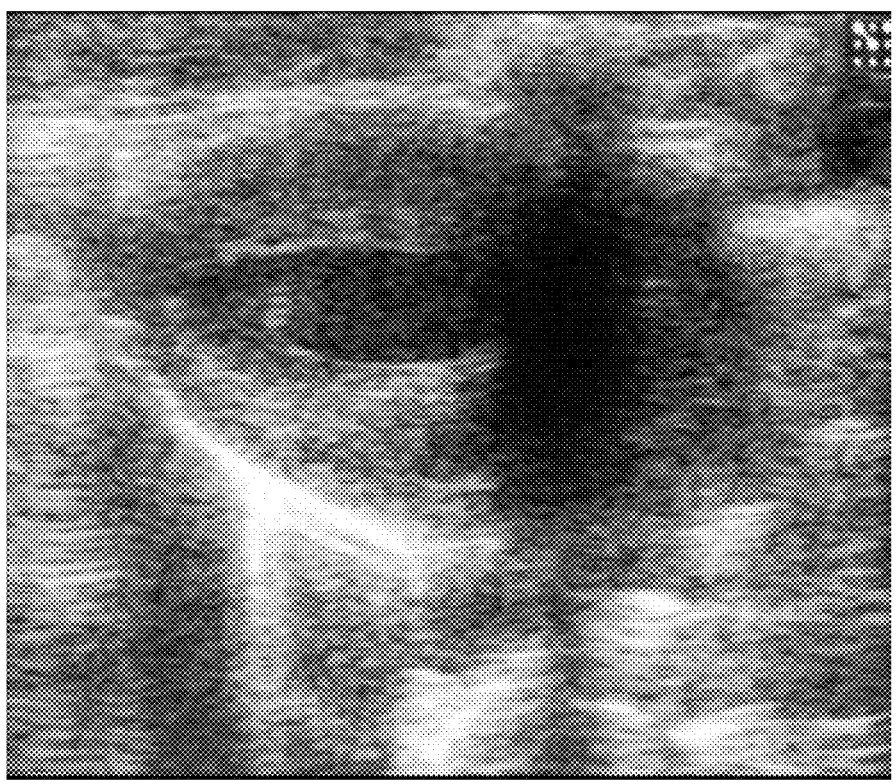

FIGS. 6A-6B are in vivo images of the left ventricle of a rat heart (long axis view). FIG. 6A was acquired prior to injection. FIG. 6B was acquired after injection of voltage-activated construct; specifically, the formulation included 50 vol % PFP droplets coated with a monolayer of polysorbate 20 (5 vol % PFP, 0.1 vol % PS20, the balance water) and 50 vol % PBS nested with a bilayer comprising 22.5 wt % DSPG, 22.5 wt % SOPC, 25% cholesterol, 30 wt % triolein and suspended in water containing low molecular weight PVA. Comparison of FIGS. 6A-6B shows echogenic enhancement of the myocardium in FIG. 6B.

Figure 7A:
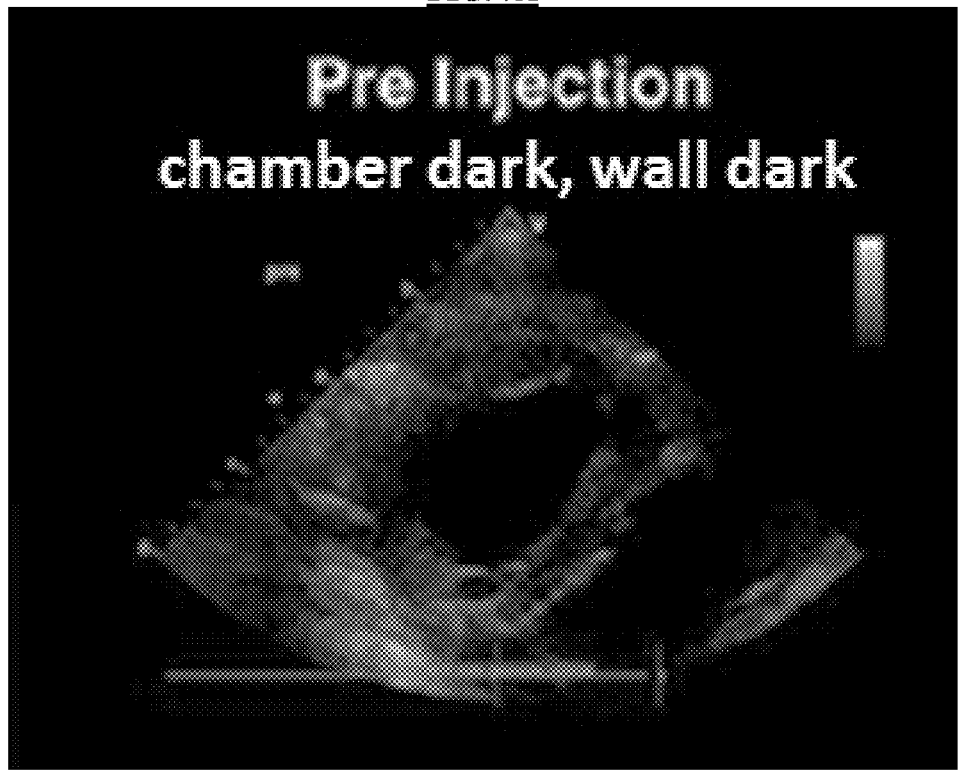
FIGS. 7A-7B are in vivo images of the left ventricle of a pig heart (short axis view).
Figure 7B:
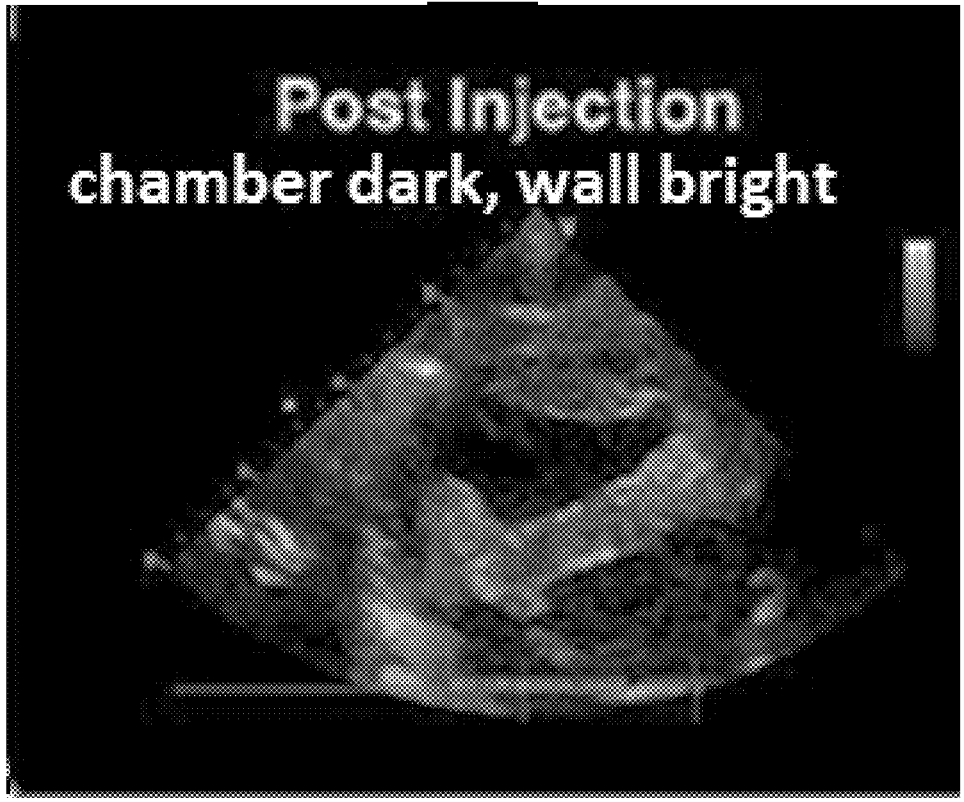
Figure 8:
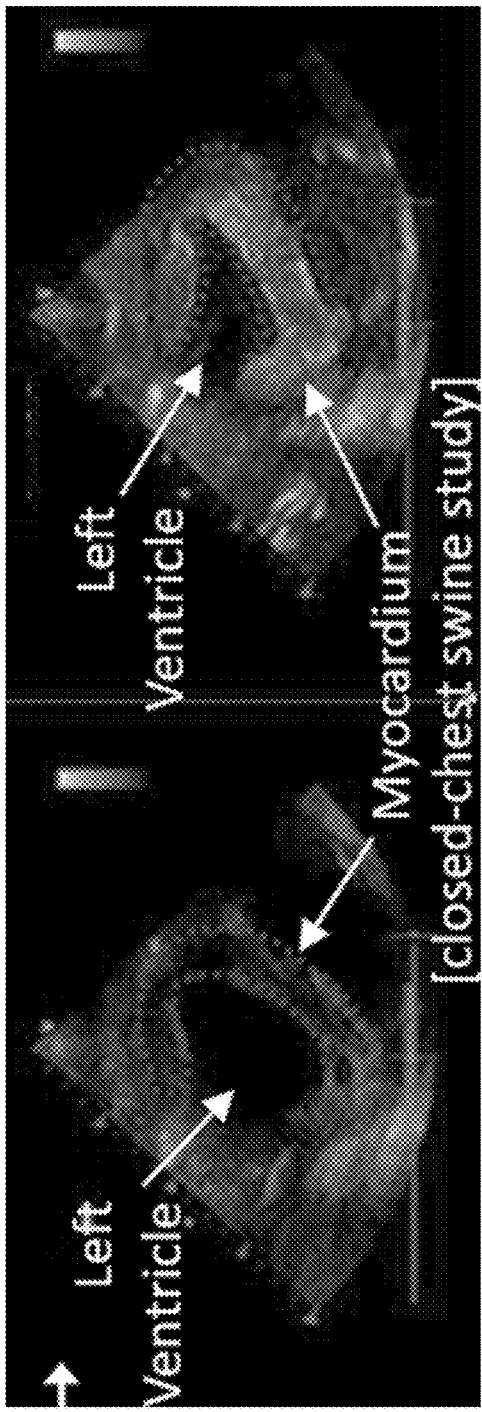
FIG. 8 are images illustrating myocardial perfusion imaging in pigs. B-mode ultrasound images showing swine left ventricle at baseline (without construct of the invention; left image) and after infusing with construct of the invention (right image). The presence of the construct gives rise to enhanced brightness within the myocardium, while leaving the ventricle unenhanced.
Figure 9:
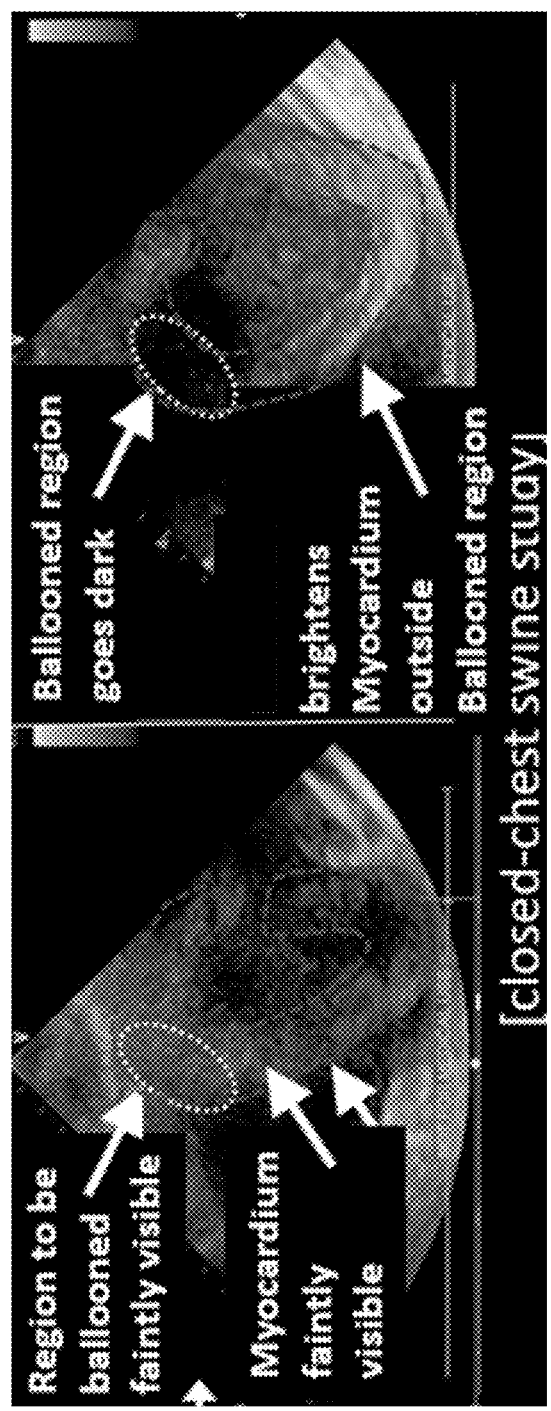
FIG. 9 are images illustrating myocardial infarct detection in pigs. B-mode ultrasound images showing swine left ventricle at baseline (without construct of the invention; left image) and after infusing construct of the invention (right image), as in FIG. 8, but where the construct was infused after a balloon had been inflated in the left anterior descending coronary artery. The presence of the construct gives rise to enhanced brightness within the myocardium but not in a region within the myocardium corresponding to the absence of perfusion, owing to the balloon. Again, the ventricle remains unenhanced.
Figure 10:
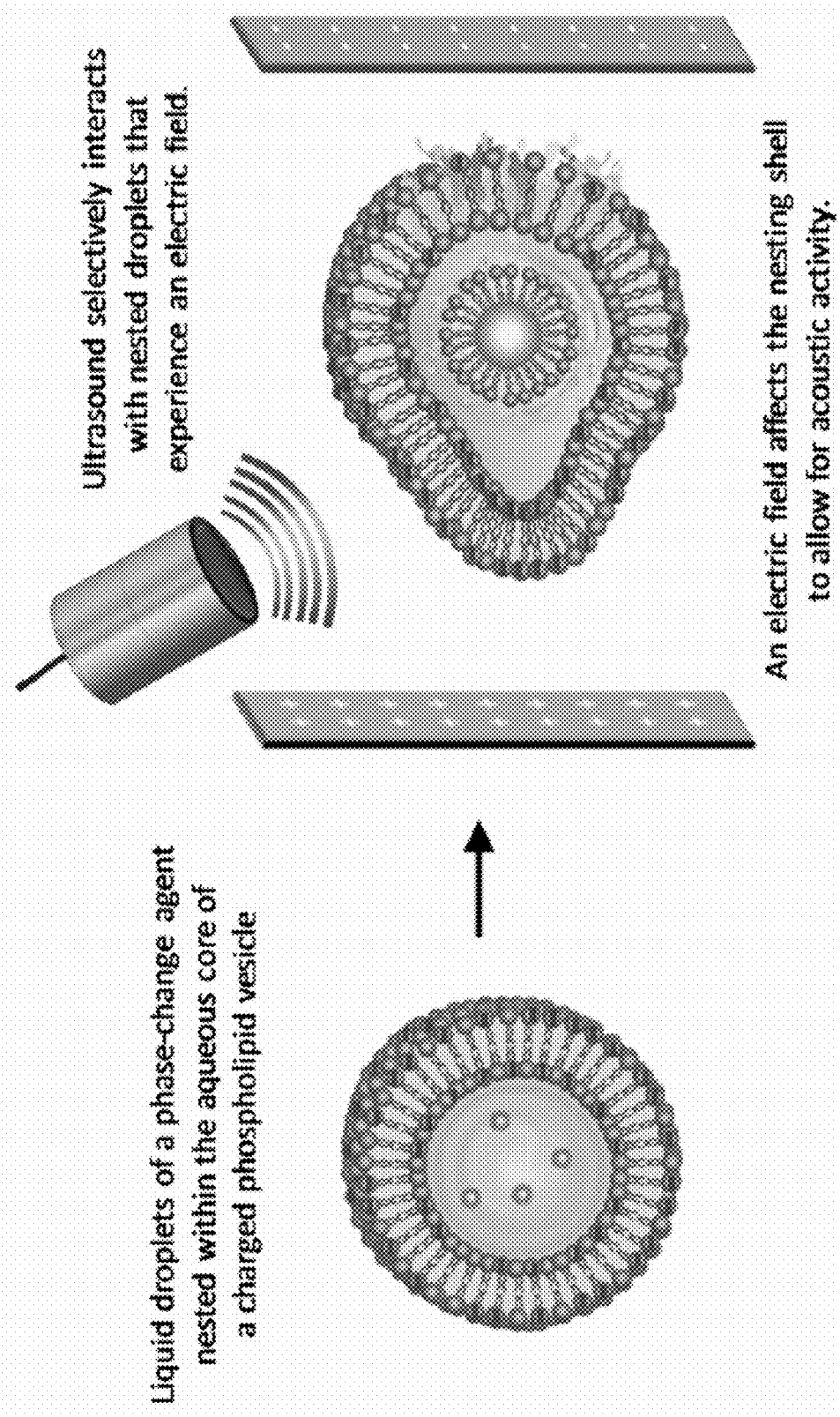
FIG. 10 illustrates a non-limiting construct of the invention. In certain embodiments, the construct comprises coated perfluorocarbon (phase change agent) droplets nested within the aqueous core of a negatively charged liposome. The nesting shell illustrated here depicts phospholipids, though other nesting shell materials can be used. In the case of phospholipid bilayer nesting shells, in certain embodiments the formulation can include additional species (e.g., cholesterol or triglycerides, or both). Moreover, phospholipid species that differ in chain length and saturation and head group type, size, and charge (cationic, anionic, zwitterionic, or non-ionic) can be used, and structures other than the ones depicted here can arise from the formulation. The dashes in the illustration indicate negative charges; (positive) counter-ions are not shown, and zeta potentials in this work should be not be confused with transmembrane potentials. The presence of an electric field influences the nesting shell, and this in turn produces increased acoustic activity. The response(s) of the nesting shell to the electric field can include, but are not limited to, shape changes, relocations and/or reorientations of domains and/or molecules, expansion, thinning, dilation, phase change, and/or phase separation. In certain embodiments, one or more of these responses lead to increased permeability of the nesting shell. In other embodiments, one or more of these responses give rise to enhanced acoustic activity, where the increased acoustic activity can arise from enhanced scattering (from the nested structure as a whole or entities within the structure, either in the shell or in the core or both; e.g., droplets can coalesce, domains can coalesce, and/or the nest can change shape) or from microbubble oscillations (where the microbubbles arise from partial or complete vaporization of the droplets or gases dissolved within the droplets).

FIGS. 7A-7B are in vivo images of the left ventricle of a pig heart (short axis view). FIG. 7A was acquired prior to injection. FIG. 7B was acquired after injection of voltage-activated agents. The formulation included 50 vol % PFP droplets coated with a monolayer of polysorbate 20 (5 vol % PFP, 0.1 vol % PS20, the balance water) and 50 vol % PBS nested with a bilayer comprising 22.5 wt % DSPG, 22.5 wt % SOPC, 25% cholesterol, 30 wt % triolein and suspended in water containing low molecular weight PVA. Comparison of FIGS. 7A-7B shows echogenic enhancement of the myocardium in FIG. 7B.

Example 3

3.1. Materials

Phospholipids, sterols and triglycerides were purchased from Avanti Polar lipids (Alabaster, Ala. USA). Perfluorocarbons were purchased from FluoroMed, L.P. (Round Rock, Tex., USA). Calcein, cobalt (II) chloride, poly vinyl alcohol (MW=27,000 & 85,000-124,000) and surfactant (polysorbate 20) were purchased from Sigma Aldrich (St. Louis, Mo.). All chemical species were used without further purification.

3.2. Methods 3.2.1. Phase-Change Agent (PCA) Nanoemulsion:

A perfluorocarbon nanoemulsion comprising perfluoropentane, surfactants and water, was prepared via probe sonication (Model UP200S Hielscher—Ultrasound Technology, Teltow, Germany) at 20 kHz and 50% amplitude. A typical batch yielded an average diameter of approximately 350 nm, measured by dynamic light scattering (NanoBrook Omni, Brookhaven Instruments Corp., Holtsville, N.Y.). An average diameter of approximately 255 nm was obtained when nanoemulsions were made with perfluorobutane via microbubble condensation. The amounts of perfluorocarbon and surfactant used to prepare the nanoemulsions were 5.00% v/v and 0.08% v/v, respectively.

3.2.2. Nesting the PCA Nanoemulsion:

Nesting proceeds via double emulsion, as described in Wallace & Wrenn, 2015, Ultrasonics 63:31-38. Different membrane components were used here to give desired nesting shell properties, and, strictly speaking, in certain non-limiting embodiments, nesting of PCAs constitutes a triple emulsion (oil in water in oil in water, or O/W/O/W).

A typical batch involved diluting 500 µL of the first emulsion (that is, the PCA nanoemulsion, O/W) with 500 µL of PBS (or, in the case of fluorescence leakage experiments, 1 mM calcein) and adding this first emulsion to 1 mL of a lipid mixture in chloroform and homogenizing using a Polytron PT3100 (Kinematica Inc., Lucerne, Switzerland) for 1 min at 12,000 RPM to give a double emulsion (O/W/O). The double emulsion was then added to 8 mL of 2% PVA (27,000 MW) in water to give a triple emulsion (O/W/O/W), which was homogenized for 2 min (again at 12,000 RPM with the Polytron PT3100). The extant triple emulsion was then added to an additional 8 mL of 2% PVA (27,000 MW) in water and placed on a magnetic stirrer for 24 h.

Two nesting shell formulations were utilized herein: Formulation I comprised 20 mol % 1,2-distearoyl-sn-glycero-3-phosphocholine (DSPC), 20 mol % 1-stearoyl-2-oleoyl-sn-glycero-3-phospho-1'-rac-glycerol (SOPG), 40 mol % cholesterol, and 20 mol % triolein; and Formulation II comprised 20 mol % 1,2-distearoyl-sn-glycero-3-phospho-1'-rac-glycerol (DSPG), 20 mol % 1-stearoyl-2-oleoyl-sn-glycero-3-phosphocholine (SOPC), 40 mol % cholesterol, and 20 mol % triolein.

The size distributions of the two nesting shell chemistries were measured with a Beckman Coulter counter (Multisizer 4E); Formulation I gave total count of $3.00 \times 10^9$ particles/mL, a mean size of 1.66 and a median size of 1.42 and Shell II gave a total count of $3.13 \times 10^9$ particles/mL, a mean size of 1.67 and a median size of 1.44

Figure 11A:
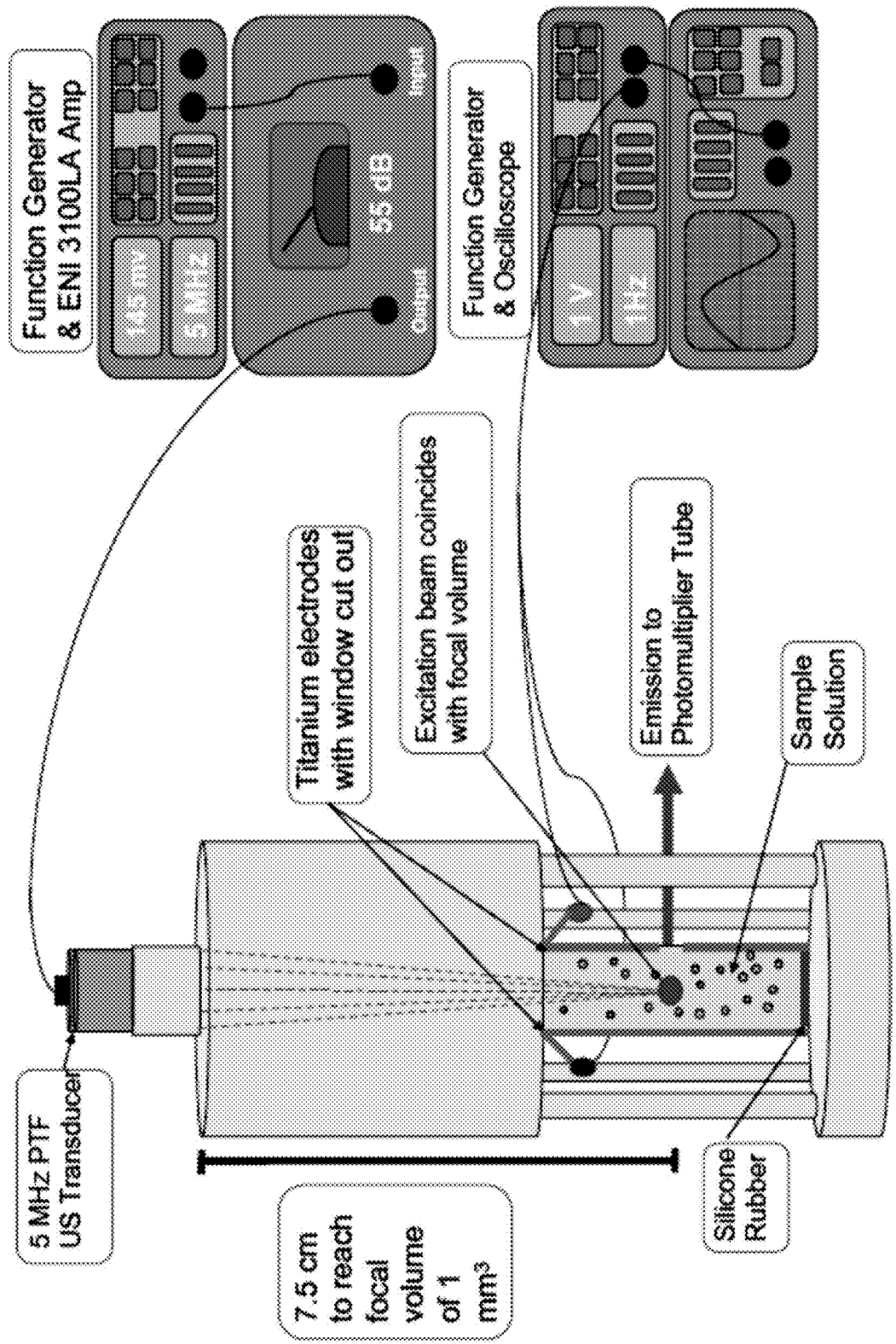
FIGS. 11A-11B illustrate custom, 3-D printed housing for live fluorescence measurements in presence of ultrasound or electric field, or both.
Figure 11B:
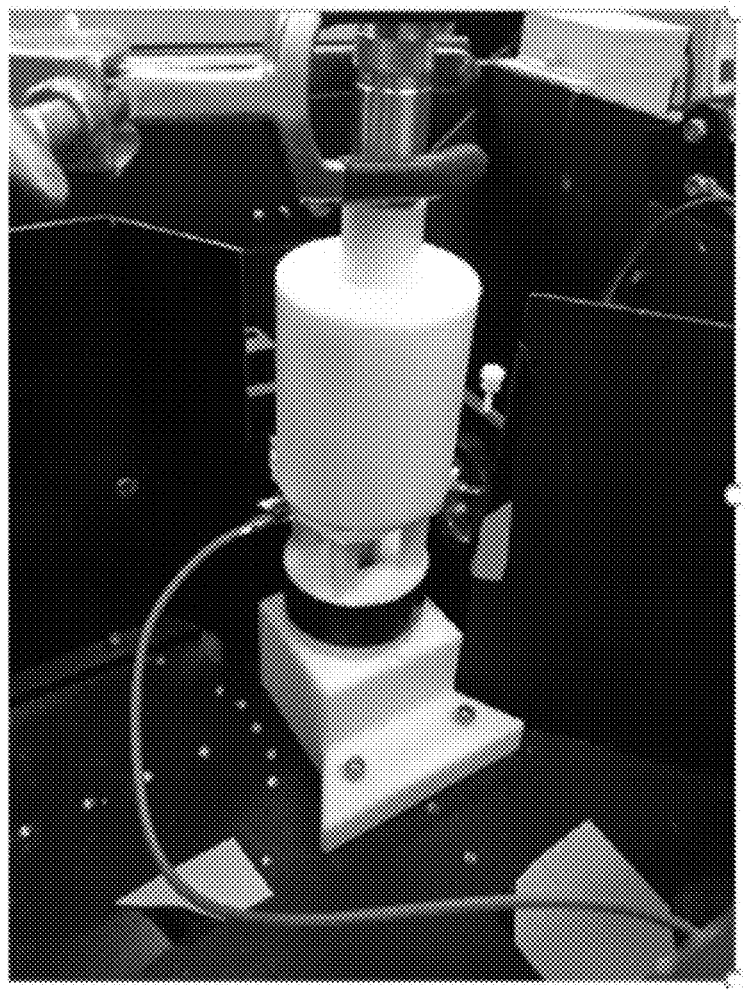

3.2.3. Fluorescence Leakage Experiments:

3.2.3.1. Home-Built (3-D Printed) Housing for Fluorescence Spectrometer:

To measure ultrasound-induced or electric field-induced, or both, fluorescence leakage in real time, a custom housing was designed using CREO Panametrics 3.0 software (PTC, Boston, Mass.) and 3-D printed on a Dimension Elite 3D Printer (Stratasys, Eden Prairie, Minn.). The home-built housing was printed in Drexel University's Machine Shop with 1.78 mm thick ABS filament (ABS P430™ Model (Ivory)) and with a solid internal structure and subsequently exposed to acetone vapor for 1 h to make the system water-tight. FIG. 11 depicts the housing, which screws into the base of a steady-state fluorimeter (A-710, Photon Technology International Inc., Birmingham, N.J.) in place of an existing cuvette holder. The basin that sits atop the pegs holds deionized water and provides a focal distance of 7.5 cm. The inside of the basin was coated with 3 layers of epoxy (to ensure that deionized water could not escape from the basin). A thin sheet of polyvinyl chloride (PVC) separates the deionized water from the sample; this sheet is acoustically transparent and does not affect the fluorescence intensity of calcein.

3.2.3.2. High Frequency Ultrasound:

Ultrasound was delivered using a 5 MHz, 7.5 cm focused ultrasound transducer (Olympus NDT, Waltham, Mass., USA), driven by an 8116A function generator (Hewlett-Packard, Palo Alto, Calif.) in series with a +55 dB ENI 3100LA power amplifier (ENI, Rochester, N.Y.). In this study, the transducer was used to deliver a desired peak negative pressures (PNP), which was measured using a calibrated HGL-0200 hydrophone (ONDA Corp., Sunnyvale, Calif.). The excitation pulse comprises 10 sinusoidal waveforms with a 40 µs pulse repetition time, corresponding to a 5% duty cycle. The ultrasound transducer is submerged into the 3-D printed ultrasound housing shown in FIG. 11 such that its focal volume is within the light path traced by the fluorescence spectrophotometer. A 0.8 cm silicone rubber sheet was placed at the bottom of the quartz cuvette to avoid standing waves.

3.2.3.3. Electric Field Parameters:

Potentials of desired voltage were applied using an Agilent 33220A function generator (Agilent, Santa Clara, Calif.)

with a sinusoidal waveform at an alternating current of 1 Hz to create electric fields of desired strength across the 99.5% titanium electrodes (Alfa Aesar, Ward Hill, Mass.) in the cuvette (1 cm width) in FIG. 11. Care was taken to minimize electrochemical reactions, and titanium was chosen as the electrode material as it is inert and highly resistive to common electrochemical reactions at low potentials. Cyclic voltammetry showed that electrochemical reactions were minimal over the voltage window of interest, and absorbance spectra confirmed that electrochemical reactions were not appreciable. Moreover, control studies with calcein and cobalt chloride in the absence of the construct of the invention and nesting shell materials ruled out electrochemical reactions as a cause for the observed changes in fluorescence intensities. A hole was punched through the electrode facing the emission monochromator to allow for transmission of light from the sample to the detector.

3.2.3.4. Calcein Assay:

Calcein leakage was measured via standard protocol (Wallace & Wrenn, 2015, Ultrasonics 63:31-38). Suspensions of nested constructs of the invention were diluted by a factor of 20× in a cobalt chloride solution. Dilution was necessary to reduce the optical density to a value less than 0.2 so as to prevent the attenuation of fluorescence intensities that would otherwise arise from light scattering via the well-known inner filter effect. The dilution was performed with cobalt chloride, the concentration of which matched calcein nearly 1:1 on a molar basis, for two non-limiting reasons: first, it minimized osmotic stress owing to variations in ionic strength across the liposomal bilayer, which could cause leakage and complicate the analysis; and second, it quenched external calcein. Samples were pipetted into quartz cuvettes, which were placed into the 3-D printed housing described elsewhere herein. Samples were exposed to varying (high-frequency ultrasound) insonation pressures, electric potentials, and combinations of the two, and fluorescence intensities recorded during exposure to the varying acoustic and electric field modalities. A sample that was not exposed to high-frequency ultrasound or electric field served as a control.

Calcein leakage was measured over 40-min intervals using the A-710 steady-state fluorescence spectrometer (Photon Technology International Inc., Birmingham, N.J.) with 2-nm slit widths, 1.0-s integration time, and 1-nm step size. Emission spectra (490-540 nm) were obtained using a 475-nm excitation wavelength. Calcein leakage (% of maximal) was calculated by Eq. (1), where $F_t$ is the fluorescence intensity of the sample at time t, $F_0$ is the initial fluorescence intensity (which defines 0% release), and $F_{100}$ is the fluorescence intensity at the conclusion of the experiment after probe sonication at high intensity and low frequency (20 kHz) (which defines 100% release).

$$\% \text{ Leakage}=(F_t-F_0)\times100/(F_{100}-F_0) \quad (1)$$

Without wishing to be limited by any theory, the leakage values reported herein do not capture any passive (meaning the absence of applied fields) leakage that might occur prior to the measurement of $F_0$, which means that the assay could potentially under-report the amounts of leakage that actually occurred. Passive leakage does not appear to be significant, however, based on observations of control samples. Specifically, the value of $F_0$, which was measured immediately (meaning within tens of seconds) after sample preparation, was not sensitive to time; control samples showed little-to-no change in fluorescence intensity for the duration of the experiment, suggesting that passive leakage, if it did occur, was complete prior to the measurement of $F_0$. If that were the case, though, then one would expect no additional leakage upon exposure to high-intensity, low frequency (20 kHz) sonication, yet the same control samples that exhibited little-to-no change in fluorescence intensity for the duration of the experiment then showed an approximately fourfold change in fluorescence intensity when sonicated. Taken together, without wishing to be limited by any theory, these observations point to a lack of appreciable leakage in the absence of applied fields.

Data is presented as an average of runs with error bars denoting standard deviations. Absorbance was measured with a Lambda 40 UV-VIS spectrometer (Perkin Elmer, Waltham, Mass.) to confirm that electrochemical reactions were not appreciable.

3.2.4. Electrophoretic Mobility:

Electrophoretic mobilities were measured on a Brookhaven NanoBrook Omni (Brookhaven Instruments Corp., Holtsville, N.Y.), which employs phase Analysis Light Scattering (PALS). The system uses a 35 mW red diode laser with a nominal wavelength of 640 nm with an effective scattering angle of 15°. Samples were diluted with DI water, and electrophoretic mobility was measured at a fixed potential of 4 V alternating at 2 Hz. Zeta potential was calculated via Eq. (2) in the Smoluchowski limit.

$$U=[(\varepsilon_r\varepsilon_0)/\eta]\xi f(\kappa a) \quad (2)$$

wherein U is electrophoretic mobility, $\varepsilon_r$ is relative permittivity of the medium, $\varepsilon_0$ is permittivity of a vacuum, $\kappa$ is inverse Debye length, $\eta$ is the viscosity of the medium, and a is the radius of the entity that moves.

It should be noted that U is the terminal velocity divided by electric field (U=v/E), and v can be calculated using Eq. (3):

$$v=QE/(6\pi\eta R) \quad (3)$$

wherein Q is the total charge of the entity, R is the radius of the charged entity, and $\eta$ is the viscosity of the medium.

3.2.5. Tissue Phantom Experiment:

Tissue Phantom Preparation:

A poly(vinyl alcohol) (PVA) cryogel phantom composed of 10 wt % PVA (85,000-124,000 MW) is used as a tissue mimicking phantom, as described by Surry, et al., 2004, Phys. Med. Biol. 49(24):5529-5546.

Figure 12A:
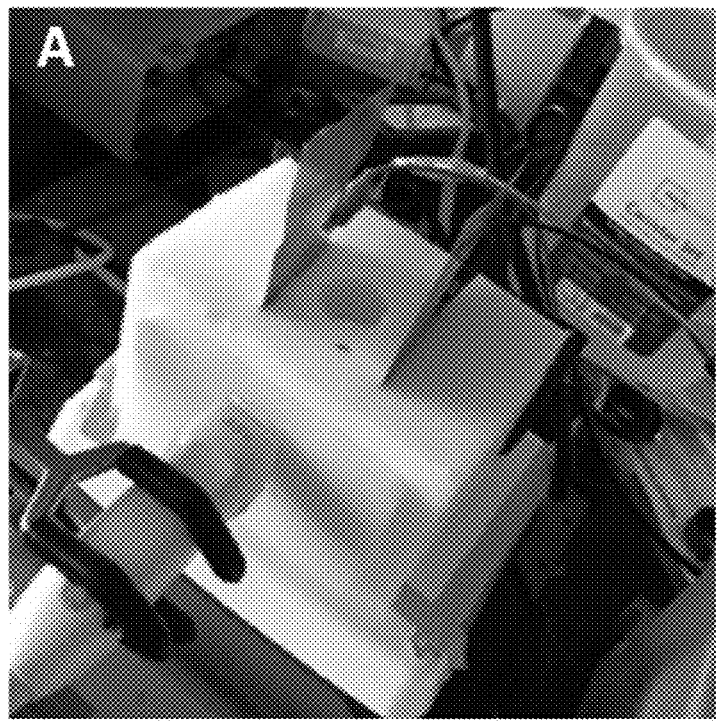
FIGS. 12A-12B illustrate tissue-mimicking phantom.

Briefly, a 1.5 L solution of 10 wt % PVA is heated to 80° C. for 12 h to allow for the polymer to solubilize. The beaker is covered with aluminum foil during the heating process to minimize water loss due to evaporation. Once the solution is fully dissolved, it is poured into a stainless-steel phantom mold that has a cylindrical sample chamber as shown in FIG. 12A and is left at room temperature for 24 h to allow air bubbles to escape. The solution then undergoes three freeze-thaw cycles so that the PVA aligns into a tight crystal structure. The speed of sound and tissue density increase with the freeze-thaw cycles; after three cycles the acoustic properties closely match human tissue, with the speed of sound in the phantom measured at 1535 m/s and the attenuation coefficients ranging from 0.075 to 0.28 dB (cm MHz)$^{-1}$. The PVA cryogel is kept at 4° C. in deionized water to avoid dehydration of the gel. A razor blade was used to cut out slices that are 5 cm in length and 8 cm in depth to allow for aluminum electrodes to be placed 6 cm apart as shown in FIG. 12A. This tissue-mimicking phantom allows for brightness studies in which intensities within the sample region are compared to intensities within the PVA tissue-mimicking region for different combinations of ultrasound and electric field parameters.

Contrast-to-Tissue Ratio (CTR):

Brightness (B) mode images were taken from a GE Vivid i (GE Medical Systems Information Technologies GmbH, Freiburg, Germany) portable clinical ultrasound machine to evaluate the contrast-to-tissue ratio (CTR) for different formulations subjected to a fixed ultrasound intensity with various electric fields. The GE Vivid i was set to 0.28 MI in the harmonic imaging mode with frequencies of 2.0 and 4.0 MHz (transmit and receive, respectively) with the use of a 2 MHz wide-band phased array transducer (GE 3S-RS) while the electric field between the electrodes was varied from 0 V/cm to 3 V/cm. The volume of the sample chamber within the PVA cryogel was 40 mL; in a typical experiment, 2 mL of a given formulation were added into 38 mL DI water. The phased array transducer was placed horizontally against the front face of the PVA cryogel with coupling gel, and the phantom was placed on a magnetic stir plate to allow mixing of the sample contents during experiments.

Figure 12B:
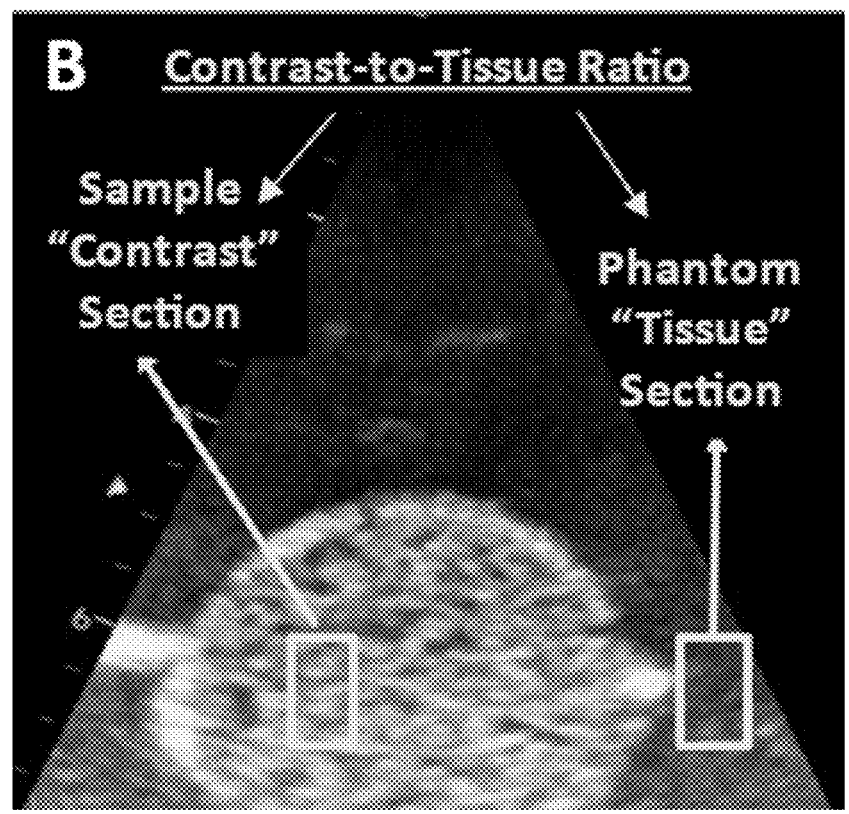

FIG. 12B shows the type of image obtained during the study and denotes two regions, the sample contrast region and the tissue-mimicking region. These regions remain the same for the entirety of the experiment. Contrast-to-tissue ratios were calculated from obtained images using a MATLAB program that digitized the recorded images, converting them to grayscale intensities ranging from 0 (black) to 255 (white). The brightness of the pixels was averaged, and the CTR value was calculated from individual brightness values via Eq. (4), where $I_C$ and $I_T$ are the grayscale intensities of the contrast and tissue regions, respectively, as calculated by the MATLAB program (Bartolomeo, et al., 2012, Bubble Sci. Eng. Technol. 4(2):78-84).

$$\text{Contrast to Tissue Ratio} = 20 \log_{10}(I_C/I_T) \quad (4)$$

3.2.6. Animal Studies:

Small Animal:

Studies were done with Sprague-Dawley rats under general anesthesia. A high-frequency, high-resolution digital imaging platform with linear array technology and Color Doppler Mode for in vivo high-resolution micro-imaging was used for (closed chest) echocardiography (VEVO® 2100 Imaging System, FUJIFILM VisualSonics Inc., Toronto, Canada). To provide appropriate resolution and depth of penetration necessary, a high-frequency transducer probe (VisualSonics MS400 with a frequency range of 18-38 MHz; operated at 21 MHz and 5% power) was utilized for the assessment of cardiovascular function and enhancement of the myocardium. In addition to the VisualSonics transducer used for imaging, the 2 MHz wide-band phased array transducer (GE 3S-RS; that is, the very same transducer that was used with the GE Vivid i in the tissue-mimicking phantom studies) was used for excitation (0.07-0.28 MI).

Large Animal:

Studies were done with swine under general anesthesia. Imaging (closed chest) and excitation were performed with the same GE Vivid i and probe that were used for the tissue-mimicking phantom studies.

Selected results of experiments are discussed herein.

Figure 13:
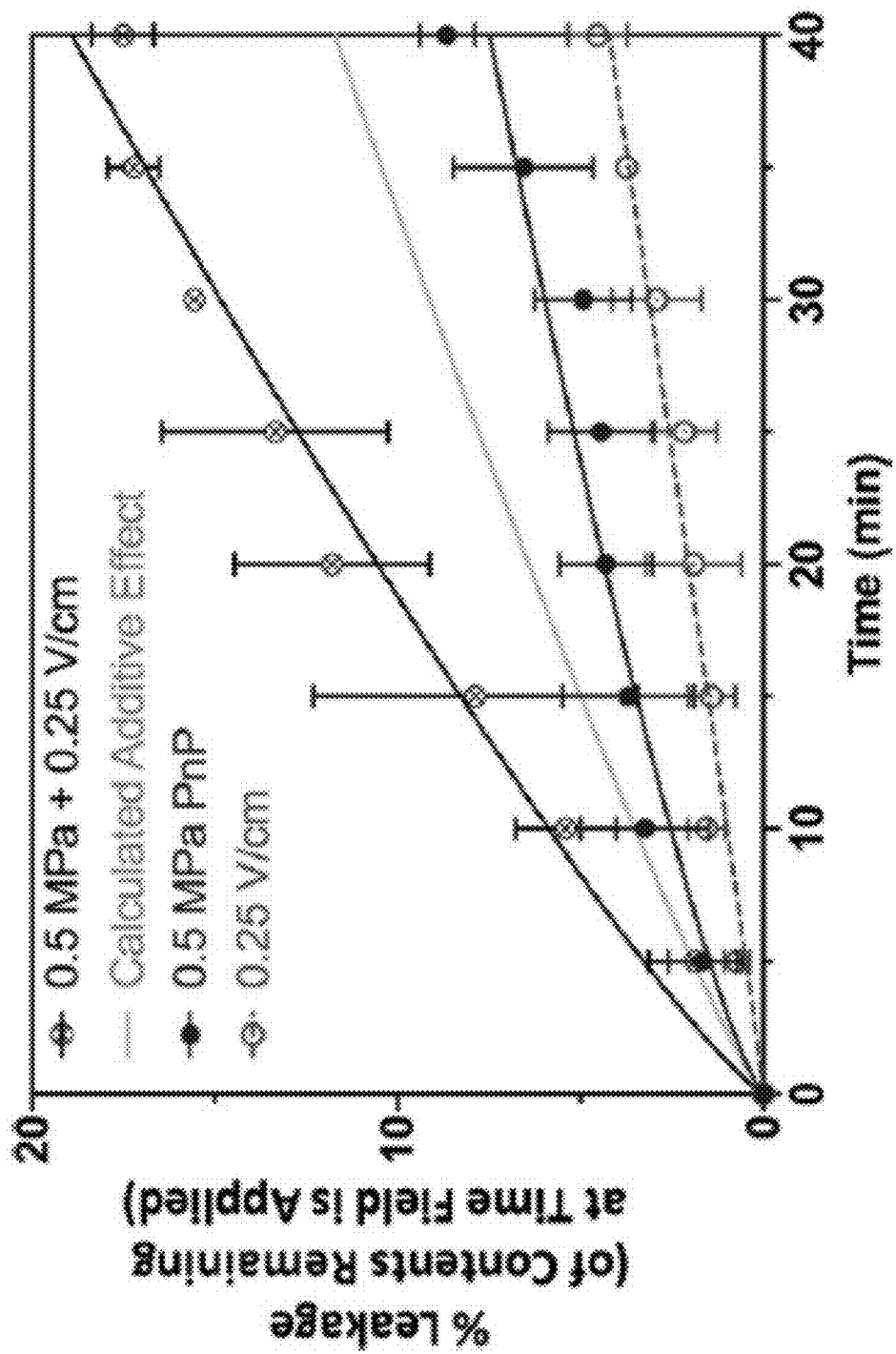
FIG. 13 illustrates synergistic Calcein release caused by ultrasound plus electric field. Temporal calcein leakage is shown for samples that were exposed to an electric field of 0.25 V/cm alone (open circles), ultrasound of 0.5 MPa PNP alone (solid circles), and both an electric field of 0.25 V/cm and ultrasound of 0.5 MPa PNP (circles filled by x's). The thin line devoid of symbols shows the "Calculated Additive Effect," which is the leakage profile obtained by adding the results of the individual modalities. The fact that the combined modalities give rise to a leakage profile that is above the "Calculated Additive Effect" indicates a synergy between ultrasound and electric field. Lines are drawn through data points to aid the eye.

In Vitro Studies:

Fluorescence Leakage Studies:

FIG. 13 shows calcein leakage from a formulation of nested constructs of the invention under three conditions: an electric field of 0.25 V/cm applied alone; ultrasound of 0.5 MPa PNP applied alone; and an electric field of 0.25 V/cm plus ultrasound of 0.5 MPa PNP applied simultaneously. Each modality alone produces measurable leakage, and the two modalities, when used in combination, exhibit a synergistic effect. This is evident if one compares the result of the combined modalities with what would be expected by simply adding the results of the individual modalities, the latter of which is depicted in FIG. 13 as a thin grey line devoid of symbols.

Figure 14:
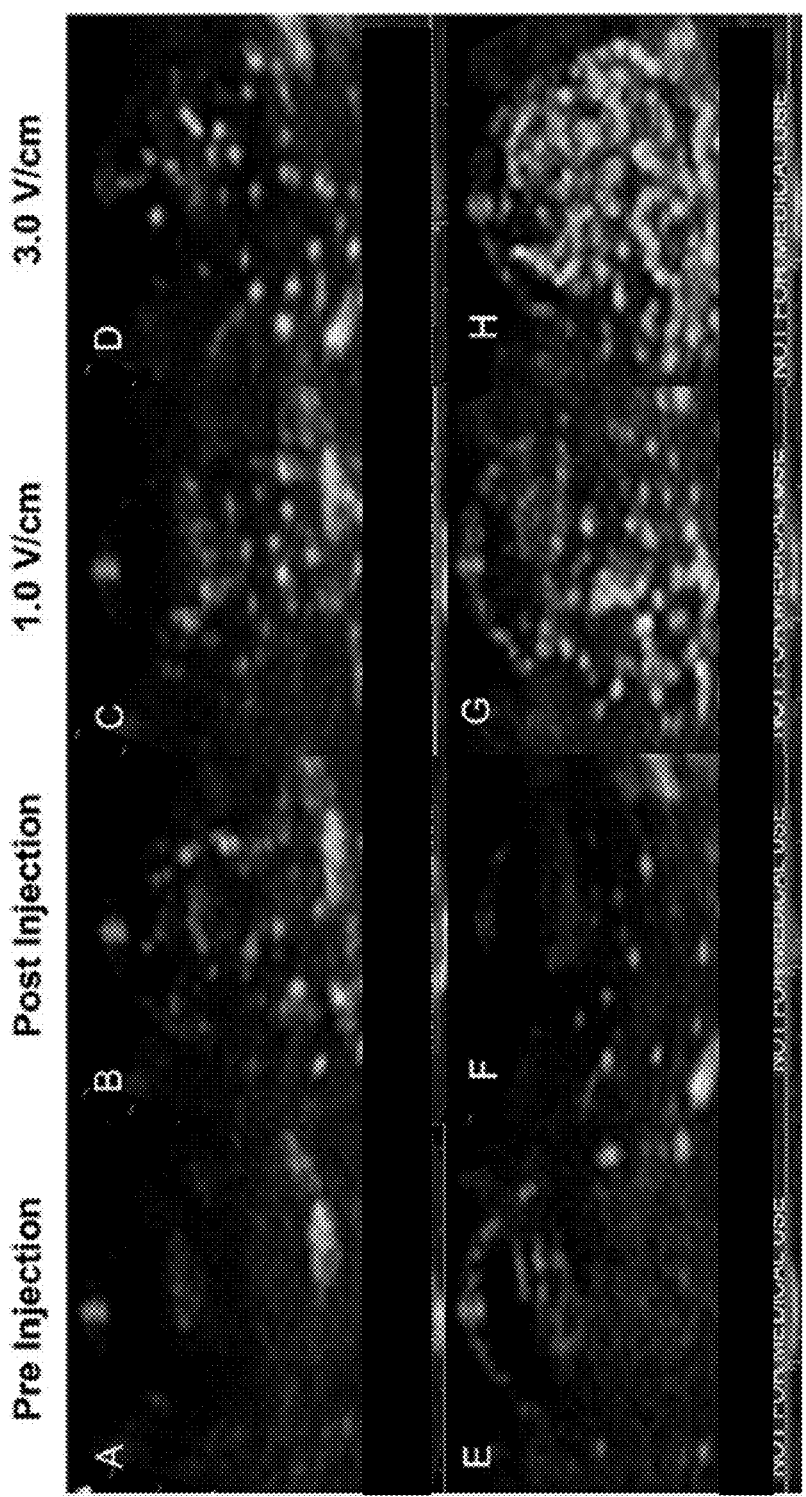
FIG. 14 illustrates voltage-activated ultrasound brightness in a tissue-mimicking phantom. The influence of an electric field on ultrasound imaging (GE Vivid 1, 0.28 MI, 2.0/4.0 MHz) brightness is shown for nesting shell chemistries I and II, which resulted in zeta potentials of ~−60 mV (top row) and ~−70 mV (bottom row), respectively. Panels A and E are images taken before the samples were added, at which point the sample chamber contained just DI water, in the absence of an electric field. Panels B and F are images taken immediately after 2 mL of sample were added to the phantom and before application of an electric field. Panels C and G are images taken when the electric field was 1.0 V/cm; image G exhibits enhanced brightness when compared with image F, whereas brightening in panel C relative to panel B is more difficult to discern. Panels D and H are images taken when the electric field was 3.0 V/cm; image H exhibits enhanced brightness relative to image G, whereas brightening in panel D relative to panel C is not evident. These qualitative brightness results are quantified via the CTR methodology and shown in FIG. 15.
Figure 15:
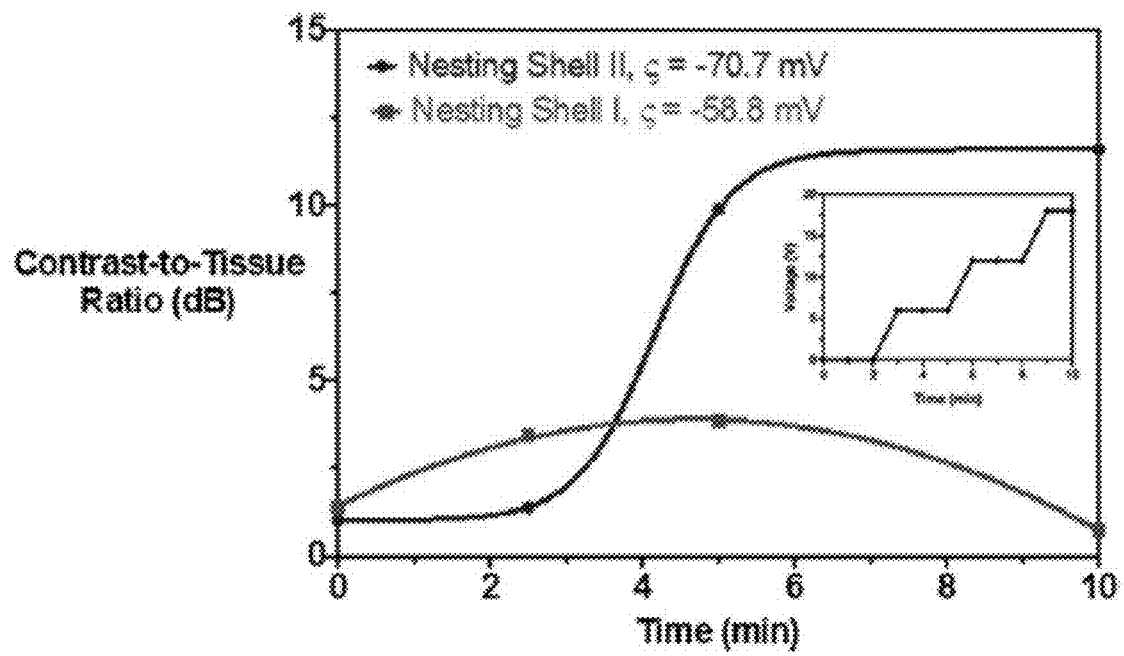
FIG. 15 illustrates voltage-activated ultrasound brightness in a tissue-mimicking phantom quantified by CTR. The results of FIG. 14 were quantified using the CTR methodology and presented as CTR versus time. The inset graph shows how the voltage difference between the two metal plates in the tissue-mimicking phantom was varied throughout the experiment.

CTR (Brightness) Studies in a Tissue-Mimicking Phantom:

FIG. 14 shows how ultrasound imaging brightness responds to an electric field for two nesting shell formulations. The first nesting shell, which gave a zeta potential of ~−60 mV, showed some visual evidence of brightening upon application of an electric field of 1.0 V/cm but did not exhibit clearly discernible (to the eye) additional brightening upon increasing the electric field strength to 3.0 V/cm. The second nesting shell, which gave a zeta potential of ~−70 mV, showed ample visual evidence of brightening, both upon application of an electric field of 1.0 V/cm and upon increasing the electric field strength to 3.0 V/cm. The qualitative visual brightness results were quantified using the CTR methodology and are given in FIG. 15, which also shows how the voltage difference between the two metal plates in the tissue-mimicking phantom was varied throughout the experiment.

Figure 16:
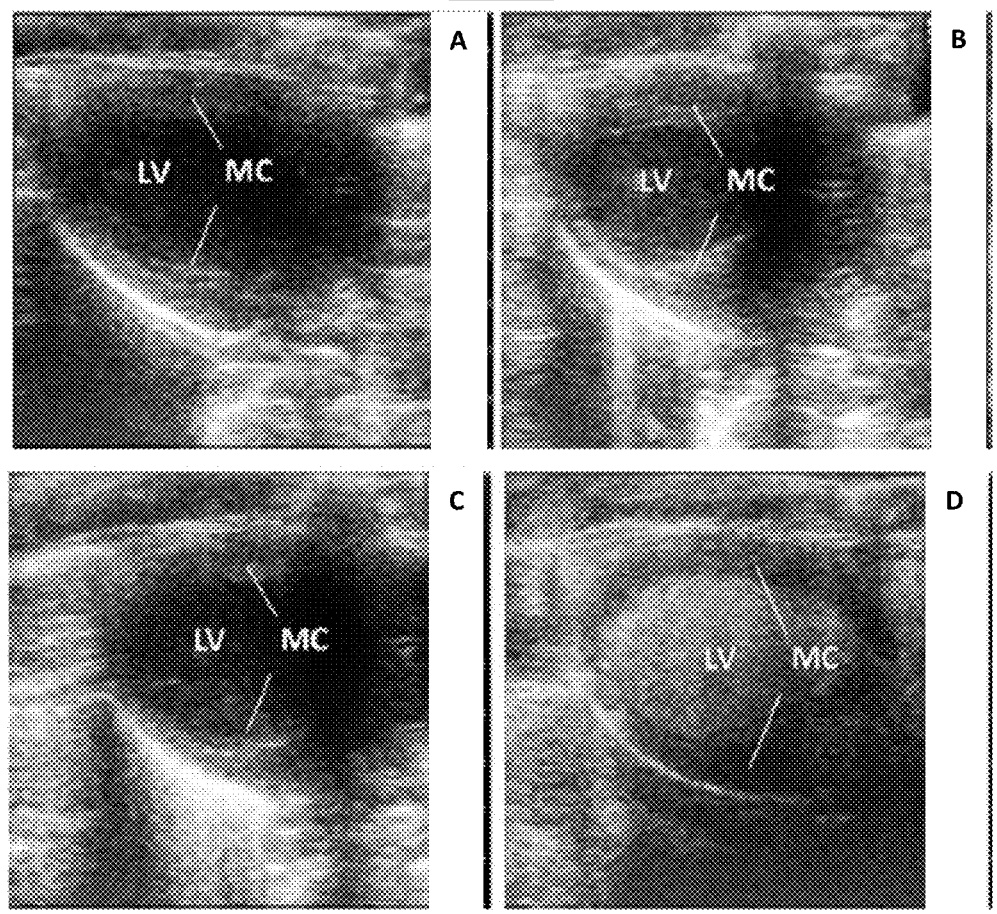
FIG. 16 illustrates voltage-activated ultrasound contrast in rat heart. B-mode images of a rat heart (closed chest) during diastole are shown for the following conditions: (A) at baseline prior to administration of any agent; (B) after administering a nested formulation with shell chemistry II; (C) after administering a nested formulation with shell chemistry I; and (D) after administering un-nested microbubbles of sulfur hexafluoride coated with a saturated phospholipid. LV=Left Ventricle, and MC=MyoCardium. Nesting shell chemistry II shows brightening of the myocardium relative to baseline, and shows some evidence of activation within the left ventricle (compare panels B and A). However, the brightening of the ventricle is far less, and the brightening of the myocardium far greater, than what is obtained with un-nested microbubbles (compare panels B and D). Nesting shell chemistry I gave a result similar to that of nesting shell chemistry II, though the effect was less pronounced (compare panels B and C).

In Vivo Studies:

Rat Studies:

FIG. 16 shows B-mode images of a rat heart (closed chest) during diastole. Panel A shows a baseline image obtained prior to administration of any agent. Panel B is an image obtained after administering a nested formulation with nesting shell chemistry II, which gave superior brightness in the tissue phantom studies. Panel C is an image obtained after administering a nested formulation with nesting shell chemistry I, and panel D is an image obtained after administering un-nested microbubbles of sulfur hexafluoride coated with a saturated phospholipid. Whereas traditional, un-nested microbubbles brighten the ventricle but not the myocardium (compare panel D with panel A), the nested constructs of the invention do the converse (e.g., compare panel B with panel A), and the level of contrast enhancement observed depends on the nesting shell formulation used (compare panel C with panel B).

Figure 17:
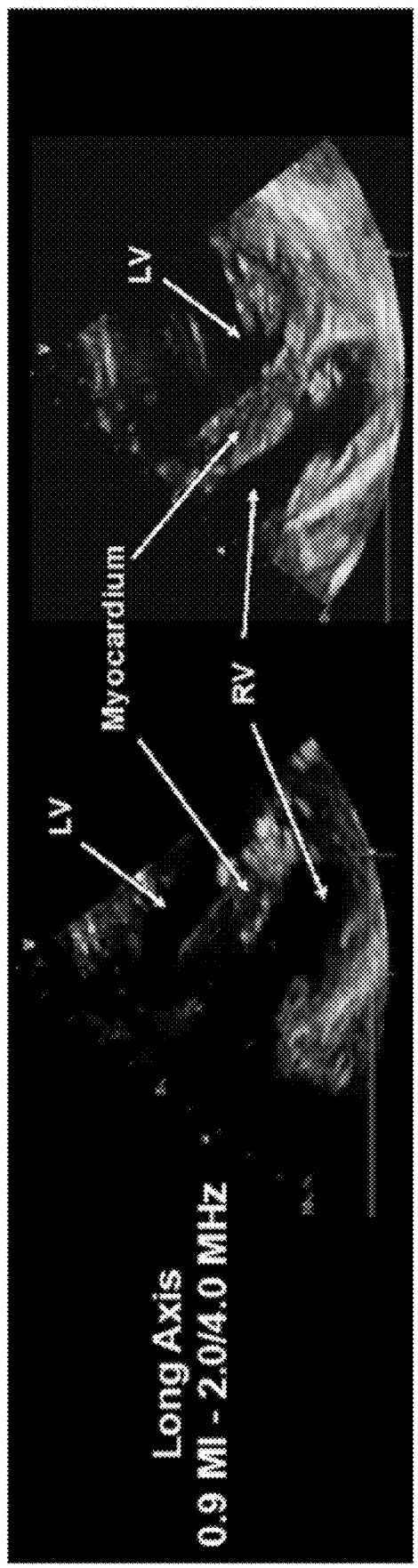
FIG. 17 illustrates voltage-activated ultrasound contrast in swine Myocardium. Long-axis view of a swine heart (closed chest) showing pre-(left image) and 30 s post-injection (right image) of nesting chemistry II. LV denotes left ventricle, and RV denotes right ventricle. The contrast enhancement between the myocardium and the left ventricle increases by 36.4 dB±0.2 upon injection of the voltage-activated construct of the invention.

Swine Studies:

FIG. 17 shows B-mode images of a pig heart (closed chest, long axis view) obtained with a GE Vivid i (the very same unit used for the tissue-mimicking phantom studies) at baseline and after administering the nested formulation with nesting shell chemistry II, which gave superior results in both the tissue-mimicking phantom and rat heart imaging studies. As was the case for the in vitro and rat studies, the nested constructs of the invention showed selective activation within the swine myocardium.

The present results illustrate an application using the constructs of the invention: myocardial perfusion imaging, that involves an endogenous electric field. In lieu of controlling the electric field, the present application takes advantage of the electric field the heart produces, which varies in time and space. The results of rat and swine studies demonstrate the feasibility and clinical relevance of such an approach, showing selective enhanced ultrasound contrast in the myocardium—where the electric field is stronger than in other regions showing less enhancement. The swine study gave the most pronounced selective contrast enhancement, as the rat study showed some activation within the left ventricle. Without wishing to be limited by any theory, this result can be explained in part by differences in attenuation, relating in part to differences in penetration depths (skin to organ), between the animals.

The in vitro studies confirm the results of the animal studies and demonstrate that voltage-sensitivity is tunable with chemistry. In particular, nesting shell formulation II exhibited a greater propensity to activate and a greater sensitivity to a change in electric field strength than nesting shell formulation I. While the two formulations had different zeta potentials, the difference in nesting shell chemistry was not merely a difference in the fraction of charged species. Thus, the type, size, valence, and location, in addition to amount, of charged species can influence the response to an electric field. Without wishing to be limited by any theory, response from each formulation can be manipulated by variations in numbers of droplets or bubbles or volumes of gas, which are known to influence echogenicity.

Evidence from in vivo studies shows the feasibility of selective activation of a voltage-sensitive ultrasound contrast agent at a fixed MI. Leakage studies in vitro and brightness studies in a tissue-mimicking phantom support the in vivo findings and demonstrate that the system is tunable. Examples of parameters that influence the sensitivity of the nested construct architecture to an electric field are nest curvature and charge, including type of charge, size of charged entity, amount of charge, and location of charge. Chemical composition of uncharged species also plays a role. The sensitivity to voltage enables activation of a subset of nested liquid perfluorocarbon droplets, namely those in the presence of an electric field, at a fixed ultrasound intensity. Reaction of the nesting shell to an electric field facilitates activation at the prevailing MI, which is otherwise insufficient to produce detectable acoustic activity. In certain non-limiting embodiments, at least partial remodeling of the bilayer due to the presence of an electric field takes place. Selective activation utilizing an electric field, regardless of mechanism, makes this voltage-sensitive phase change agent well-suited for myocardial perfusion imaging.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition, comprising:

(a) a liquid core comprising insoluble liquid droplets, wherein the insoluble liquid droplets are dispersed in an inner core liquid and are coated with a surfactant; and (b) a bilayer nesting shell surrounding the liquid core, wherein the bilayer nesting shell comprises a phospholipid or a polymer, wherein the nesting shell is more permeable to the inner core liquid in the presence of an electric field than in the absence of an electric field.

2. The composition of claim 1, wherein the nesting shell further comprises a triglyceride.

3. The composition of claim 2, wherein the triglyceride is triolein.

4. The composition of claim 1, wherein the inner core liquid comprises water.

5. The composition of claim 1, wherein the nesting shell further comprises cholesterol.

6. The composition of claim 1, wherein the nesting shell comprises a saturated phospholipid and an unsaturated phospholipid, wherein one of the phospholipids is neutral and the other phospholipidis charged.

7. The composition of claim 6, wherein the saturated phospholipid is distearoylphosphatidylcholine (DSPC), distearoylphosphatidylglycerol (DSPG), or a mixture thereof.

8. The composition of claim 6, wherein the unsaturated phospholipid is stearoyl, oleoylphosphatidylglycerol (SOPG), stearoyl, oleoylphosphatidylcholine (SOPC), or a mixture thereof.

9. The composition of claim 1, wherein the insoluble liquid droplets comprise a perfluorocarbon.

10. The composition of claim 9, wherein the perfluorocarbon is selected from the group consisting of perfluoropentane, perfluorobutane, perfluoropentane, perfluorohexane, or a mixture thereof.

11. The composition of claim 9, wherein the insoluble liquid droplets comprise perfluorobutane.

12. The composition of claim 1, wherein the surfactant is polysorbate 20.

13. The composition of claim 1, wherein the composition further comprises a drug.

14. A composition for imaging a portion of a subject's heart, the composition comprising:

(a) a liquid core, comprising insoluble liquid droplets, wherein the insoluble liquid droplets are dispersed in an inner core liquid and are coated with a surfactant; and (b) a bilayer nesting shell surrounding the liquid core, wherein the bilayer nesting shell comprises a phospholipid;

wherein the nesting shell is more permeable to the inner core liquid in depolarizing heart tissue.

15. The composition of claim 14, wherein the nesting shell further comprises a triglyceride.

16. The composition of claim 14, wherein the nesting shell further comprises cholesterol.

17. The composition of claim 14, wherein the nesting shell comprises a saturated phospholipid and an unsaturated phospholipid, wherein one of the phospholipids is neutral and the other phospholipid is charged.

18. The composition of claim 17, wherein the saturated phospholipid is distearoylphosphatidylcholine (DSPC), distearoylphosphatidylglycerol (DSPG), or a mixture thereof.

19. The composition of claim 17, wherein the unsaturated phospholipid is stearoyl, oleoylphosphatidylglycerol (SOPG), stearoyl, oleoylphosphatidylcholine (SOPC), or a mixture thereof.

20. The composition of claim 17, wherein the saturated phospholipid is distearoylphosphatidylcholine (DSPC) and the unsaturated phospholipid is stearoyl, oleoylphosphatidylglycerol (SOPG).

21. The composition of claim 17, wherein the saturated phospholipid is distearoylphosphatidylglycerol (DSPG) and the unsaturated phospholipid is stearoyl, oleoylphosphatidylcholine (SOPC).

22. The composition of claim 14, wherein the insoluble liquid droplets comprise a liquid perfluorocarbon.

23. The composition of claim 22, wherein the liquid perfluorocarbon is selected from the group consisting of perfluoropentane, perfluorobutane, perfluoropentane, perfluorohexane, or a mixture thereof.

24. The composition of claim 17, wherein the nesting shell comprises: about 10-32.5 wt % saturated phospholipid, and about 10-32.5 wt % unsaturated phospholipid.

* * * * *